United States Patent
Li et al.

(10) Patent No.: US 7,340,938 B2
(45) Date of Patent: Mar. 11, 2008

(54) MIS-BASED SENSORS WITH HYDROGEN SELECTIVITY

(75) Inventors: Dongmei Li, Boulder, CO (US); J. William Medlin, Boulder, CO (US); Anthony H. McDaniel, Livermore, CA (US); Robert J. Bastasz, Livermore, CA (US)

(73) Assignees: The Regents of the University of Colorado, Boulder, CO (US); The United States of America as represented by The United States Department of Energy, Washington, DC (US)

(*) Notice: Subject to any disclaimer, the term of this patent is extended or adjusted under 35 U.S.C. 154(b) by 0 days.

(21) Appl. No.: 11/361,310

(22) Filed: Feb. 24, 2006

(65) Prior Publication Data

US 2006/0196246 A1    Sep. 7, 2006

Related U.S. Application Data

(60) Provisional application No. 60/656,559, filed on Feb. 24, 2005.

(51) Int. Cl.
G01N 7/00 (2006.01)
(52) U.S. Cl. ...................................................... 73/23.2
(58) Field of Classification Search ................ 73/23.2
See application file for complete search history.

(56) References Cited

U.S. PATENT DOCUMENTS

| | | | | |
|---|---|---|---|---|
| 5,698,771 A | * | 12/1997 | Shields et al. | 73/31.05 |
| 6,041,643 A | * | 3/2000 | Stokes et al. | 73/31.06 |
| 6,155,100 A | * | 12/2000 | Stokes et al. | 73/31.06 |
| 6,182,500 B1 | * | 2/2001 | Stokes et al. | 73/31.06 |
| 6,202,473 B1 | * | 3/2001 | Stokes et al. | 73/31.06 |
| 6,450,007 B1 | * | 9/2002 | O'Connor | 73/23.2 |
| 6,539,774 B1 | * | 4/2003 | Zinck et al. | 73/23.2 |
| 6,634,213 B1 | | 10/2003 | O'Connor et al. | |
| 6,730,270 B1 | * | 5/2004 | O'Connor | 422/98 |
| 6,895,805 B2 | | 5/2005 | Hoagland | |
| 2004/0023087 A1 | * | 2/2004 | Redmond | 429/19 |

OTHER PUBLICATIONS

Åbom et al. (2002) "Thin Oxide Films as Surface Modifiers of MIS Field Effect Gas Sensors," *Sens. Actuators B* 85:109-119.
Armgarth et al. (Oct. 1, 1982) "Palladium and Platinum Gate Metal-Oxide-Semiconductor Capacitors in Hydrogen and Oxygen Mixtures," *Appl. Phys. Lett.* 41:654-655.
Baker, R. (2000) *Membrane Technology and Applications*, New York, McGraw-Hill, pp. 312.

(Continued)

*Primary Examiner*—Hezron Williams
*Assistant Examiner*—Rodney Frank
(74) *Attorney, Agent, or Firm*—Greenlee, Winner and Sullivan, P.C.

(57) ABSTRACT

The invention provides hydrogen selective metal-insulator-semiconductor sensors which include a layer of hydrogen selective material. The hydrogen selective material can be polyimide layer having a thickness between 200 and 800 nm. Suitable polyimide materials include reaction products of benzophenone tetracarboxylic dianhydride 4,4-oxydianiline m-phenylene diamine and other structurally similar materials.

23 Claims, 11 Drawing Sheets

OTHER PUBLICATIONS

Borodzinski et al. (1997) "Surface Heterogeneity of Supported Pd Catalyst for the Hydrogenation of Acetylene-Ethylene Mixtures," *Langmuir* 13:883-887.

Dannetun et al. (1986) "Dehydrogenation of Acetyl and Ethylene Studied on Clean and Oxygen Covered Palladium Surfaces," *Surf. Sci.* 173:148-159.

Eriksson et al. (1998) "Real Time Measurements of Hydrogen Dessorption and Absorption During CO Exposures of Pd: Hydrogen Sticking and Dissolution," *Appl. Surf. Sci.* 133:89-97.

Eriksson et al. (1997) "The Influence of CO on the Response of Hydrogen Sensitive Pd-MOS Devices," *Sens. Actuators B* 42:217-223.

Ghosh et al. (1996) "Polyimides for Gas Separation," In; *Polyimides, Fundamentals and Applications*, Langsam, M. ed., New York, Marcel Dekker, Inc., p. 721-736.

Hedborg et al. (1993) "Some Studies of Molecularly-Imprinted Polymer Membranes in Combination ith Field-Effect Devices," *Sens. Actuators A* 37-38:796-799.

Hedborg et al. (1992) "Polymer Membranes for Modification of the Selectivity of Field-Effect Gas Sensors," *Sensors and Actuators B* 7:661-664.

Hughes et al. (1997) "Hydrogen Sensing in Vacuum Systems with Catalytic Field Plae MNOS Capacitors," *Appl. Surf. Sci.* 115:74-79.

Iacona et al. (Apr. 1991) "Interfacial Reactions in Polymide Metal Systems," *J. Mater. Res.* 6:861.

Jeong et al. (Published on Web Sep. 9, 2004) "Fabrication of Polymer/Selective-Flake Nanocomposite Membranes and Their Use in Gas Separation," *Chem. Mater.* 16:3838-3845.

Johansson et al. (Jul. 1, 1998) "Bridging the Pressure Gap for Palladium Metal-Insulator-Semiconductor Hydrogen Sensors in Oxygen Containing Environments," *J. Appl. Phys.* 84:44-51.

Kaichev et al. (Published on web Mar. 25, 2003) "High-Pressure Studies of CO Adsorption on Pd(1 1 1) by X-ray Photoelectron Spectroscopy and Sum-Frequency Generation," *J. Phys. Chem. B* 107:3522-3527.

Koros et al. (1993) "Membrane-Based Gas Separation," *J. Membr. Sci.* 83:1-80.

Lee et al. (Published on Web Jun. 26, 2002) "Preparation and Characterization of $SiO_2$ Composite Membranes for Purification of Hydrogen for PEMFC," *Industrial. Eng. Chem. Res.* 41:3594-3600.

Lee et al. (2003) "Preparation and Characterization of $SiO_2$ Composite Membrane for Purification of Hydrogen from Methynol Steam Reforming as an Energy Carrier System for PEMFC," *Separation and Purification Technol.* 32:45-50.

Li et al. (Published on Web Jun. 7, 2006) "Application of Polymer-Coated MIS Sensors in Detection of Dissolved Hydrogen," *Appl. Phys. Lett.* 88:233507.

Li et al. (Published on Web Oct. 13, 2005) "Effects of a Polyimide Coating on the Hydrogen Selectivity of MIS Sensors," *Sens. Actuators B* 115:86-92.

Liu et al. (Apr. 29, 1999) "Gas Permeability and Permselectivity of Photochemically Crosslinked Copolimides," *J. Appl. Poly. Sci.* 73(4):521-526.

Lundstrom, I. (1996) "Why Bother about Gas-Sensitive Field-Effect Devices," *Sens. Actuators A* 56:75-82.

Lundstrom, I. (1981) "Hydrogen Sensitive Mos-Structures: 1. Principles and Applications," *Sens. Actuators* 1:403-426.

Lundstrom, I. (1981) "Hydrogen Sensitive Mos-Structures: 2. Characterization," *Sens. Actuators* 2:105-138.

Medlin et al. (Feb. 15, 2003) "Effects of Competitive CO Adsorption on the Hydrogen Response of MIS Sensors: The Role of Metal Film Morphology," *J. Appl. Phys.* 93:2267-2274.

Medlin et al. (2003) "The Response of Palladium Metal0Insulator-Semiconductor Devices to Hydrogen-Oxygen Mixtures: Comparisons Between Kinetic Models and Experiment," *Sens. Actuators B* 96:290-297.

Medlin et al. (Published on Web Dec. 10, 2002) "A Theoretical Study of the Adsorption of Acetylene on the (1 1 1) Surfaces of Pd, Pt, Ni, and Rh," *J. Phys. Chem. B* 107:217-223.

Monnier et al. (2000) "Selective Isomerization of 2,5-Dihydrofuran to 2,3-Dihydrofuran Using CO-Modified, Supported Pd Catalysis," *Appl. Catal. A* 194-195:463-474.

Robins, I. (1993) "Drift Effects in Transition-Metal Gate MOS and MISFETs," *Sens. Actuators B* 15:238.

Rose et al. (2002) "Ordered Structures of CO on Pd(1 1 1) Studied by STM," *Surf. Sci.* 512:48-60.

Sawada et al. (Published on Web Sep. 26, 1998) "Synthesis, Characterization, and Optical Properties of Metal-Containing Fluorinated Polyimide Films," *Chem. Mater.* 10:3368-3378.

Stacchiola et al. (2002) "Ethylene Adsorption on Pd (1 1 1) Studied Using Infrared Reflection-Adsorption Spectroscopy," *Surf. Sci.* 511:215-228.

Stern et al. (1989) "Structure Permeability Relationships of Polyimide Membranes—Applications to the Separation of Gas-Mixtures," *J. Poly. Sci. A. Poly. Chem.* 27(9):1887-1909.

Sullivan et al. (Published on Web Dec. 5, 2002) "Ultrathin, Gas-Selective Polyimide membranes Prepared from Multilayer Polyelectrolyte Films," *Chem. Mater.* 15:281-287.

Tanaka et al. (1992) "Permeability and Permselectivity of Gases in Fluorinated and Non-Fluorinated Polyimides," *Polymer* 33(3):585-592.

Tanaka et al. (1989) "Gas-Permeability and Permselectivity in Polyimides Based on 3,3',4,4'-Biphenyltetracarboxylic Dianhydride," *J. Membr. Sci.* 47(1-2):203-215.

Tanaka et al. (1992) "Effect of Methyl Substituents on Permeability and Permselectivity of Gases in Polyimides Prepared from Methyl-Substituted Phenylenediamines," *J. Poly. Sci. B. Poly. Phys.* 30(8):907-914.

Watwe et al. (Mar. 8, 2001) "Density Functional Theory Studies of the Adsorption of Ethylene and Oxygen on Pt(1 1 1) and Pt3Sn(1 1 1)," *J. Chem. Phys.* 114(10):4663-4668.

* cited by examiner

DABP p,p' m,m'

DADPS

Benzidine p,p' AP BAA

BAP p,p' APB 2,6 TDA

Mesitylene diamine

|  | R₁ | R₂ |
|---|---|---|
| 4H Fluorenyl | H | H |
| 2H 2F Fluorenyl | H | F |
| 2H 2Me Fluorenyl | H | Me |
| 4Me Fluorenyl | Me | Me |
| 2Me 2ipro Fluorenyl | Me | Ipro |

|  | R₁ | R₂ |
|---|---|---|
| 2Me 2Et MDA | Me | Et |
| 2Me 2Ipro MDA | Me | Ipro |
| MDA | H | H |
| 2H 2ipro MDA | H | Ipro |
| 2H 2t-bu MDA | H | t-bu |
| 2H 2F MDA | H | F |
| 4Me MDA | Me | Me |
| 4Et MDA | Et | Et |
| 4ipro MDA | ipro | ipro |

Fig. 3A
Fig. 3B
Sensor layout
Device structure
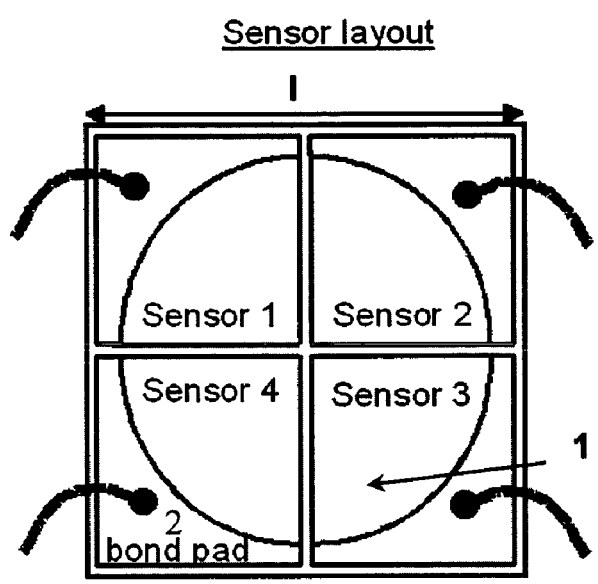
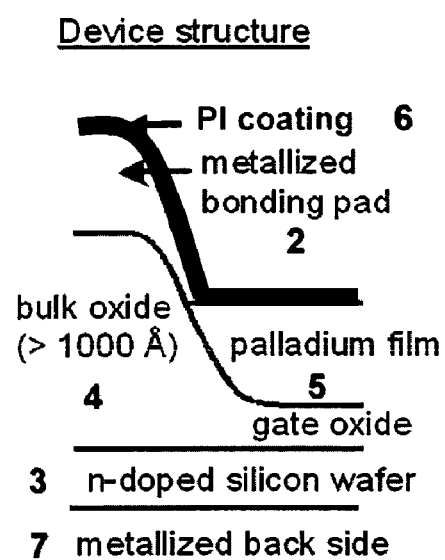

MIS-BASED SENSORS WITH HYDROGEN SELECTIVITY

CROSS-REFERENCE TO RELATED APPLICATIONS

This application claims the benefit of U.S. Provisional Application No. 60/656,559, filed Feb. 24, 2005, which is hereby incorporated by reference to the extent not inconsistent with the disclosure herein.

ACKNOWLEDGEMENT OF GOVERNMENT SUPPORT

This invention was funded, at least in part, by the United States Department of Energy under grant number DE-AC04-94AL85000. The U.S. government has certain rights in this invention.

BACKGROUND OF THE INVENTION

This invention is in the field of metal-insulator-semiconductor (MIS) sensors, in particular, MIS-based sensors with improved selectivity for hydrogen. Real-time hydrogen ($H_2$) detection is important in various industrial settings. For example, $H_2$ detection in the headspace of distribution transformers is an indicator of undesirable partial discharge.

The detection of gases dissolved in liquids is also an important problem for many applications. (Hedborg, E.; Winquist, F.; Lundstrom, I.; Andersson, L. I.; Mosbach, K., Some studies of molecularly-imprinted polymer membranes in combination with field-effect devices, *Sens. Actuators A* 1993, 37-8, 796). For example, faults may occur when oil-filled electrical equipment is subjected to thermal or electrical stresses, which break down the oil and generate "fault gases".

Solid-state metal-insulator-semiconductor (MIS) sensors are excellent candidates for this purpose. These sensors are prepared by depositing a film of catalytic metal onto a thin layer of gate insulator material that has been grown on a semiconductor substrate. If the insulator is silicon dioxide, these sensors may also be termed metal-silicon dioxide-semiconductor (MOS) or thin-film metal-silicon dioxide-semiconductor (TMOS) sensors.

The basic $H_2$ sensing mechanism for MIS devices has been described in pioneering works by Lundström and coworkers. To provide a brief description, gas-phase $H_2$ dissociates on the surface of the catalytic metal to form H atoms. These H atoms then rapidly diffuse through the metal film to the metal-insulator interface, where they are preferentially trapped in stabilized adsorption sites. The layer of interfacial hydrogen created by this process exists in a dipole layer, creating an additional voltage drop across the MIS sensor that can be measured as either a voltage shift in the capacitance-voltage (C-V) curve of a capacitor, or in the current-voltage characteristic of a diode or transistor.

Previous work has proven that MIS sensors that are highly responsive to $H_2$ can be reproducibly prepared. For example, MIS sensors are capable of detecting $H_2$ concentrations in the parts per billion range. However, the development of MIS sensors for industrial applications is still challenging because of the cross-sensitivity to other gases, such as carbon monoxide (CO), ethylene ($C_2H_4$), acetylene ($C_2H_2$) and potentially oxygen ($O_2$). Some of these gases, such as ethylene, are hydrogen containing gases which can dissociate to form hydrogen which can be directly detected by the sensor. Other gases are not directly detected by the sensor, but can influence the response of the sensor to hydrogen. For example, carbon monoxide can affect the response of the sensor to hydrogen and other gases through strong competitive adsorption on the catalytic metal surface. As another example, oxygen can affect the response of the sensor to hydrogen through water forming reactions. Water forming reactions between adsorbed H and O on the catalytic metal surface can consume H, leading to a substantially decreased sensor response.

Gas sensors including polymer coatings have been reported in the patent literature. U.S. Pat. No. 6,634,213 to O'Connor et al. reports a hydrogen permeable protective coating for a single-chip hydrogen sensor. Organic coatings are stated to be preferred; FLARE™ and HOSP™ spin-on coatings are specifically mentioned. U.S. Pat. No. 6,182,500 to Stokes et al. reports a protective layer disposed on the catalytic metal gate of a gas sensor. A thin film of hydrophobic polytetrafluoroethylene is mentioned as an exemplary material for the protective layer. The protective layer is stated to improve the sensor's sensitivity by allowing only certain gases to pass through and interact with the catalytic metal gate layer. Amounts of other gases, as well as foreign matter, that pass through the protective layer are stated to be reduced, and even prevented, from passing through. U.S. Pat. No. 6,895,805 to Hoagland reports a hydrogen gas indicator that comprises a gas diffusion barrier coupled to a catalyst material of a gas sensor; the gas sensor does not appear to be a metal-insulator-semiconductor sensor. The gas diffusion barrier is stated to allow selectively permeable diffusion of molecular hydrogen gas or atomic hydrogen gas.

There remains a need in the art for MIS sensors having improved hydrogen selectivity.

SUMMARY OF THE INVENTION

The present invention provides a hydrogen-selective MIS gas sensor. For a hydrogen selective sensor, changes in sensor output due to changes in hydrogen concentration are larger than changes in sensor output due to equivalent concentration changes of other gases. In an embodiment, the change in sensor output due to a change in hydrogen concentration is at least 400 times greater than the change in sensor output due to a subsequent change in concentration of hydrocarbon gases such as methane, ethylene and acetylene. In another embodiment, the change in sensor output due to a change in hydrogen concentration is at least 10 times greater than the change in sensor output due to a prior change in concentration of hydrocarbon gases such as methane, ethylene and acetylene.

In the present invention, hydrogen-selectivity is achieved by attaching a layer of hydrogen selective material to the top surface of the layer of catalytic material of a MIS sensor. The hydrogen selective material is selected to have high selectivity for hydrogen compared to the other gas (or gases) of interest that the uncoated MIS sensor may also be sensitive to. The thickness of the layer of hydrogen selective material is also important. The hydrogen selective layer should be thick enough so that hydrogen selectivity of the sensor is observed, while still providing a reasonable signal level and a reasonable response time. In an embodiment where the hydrogen selective layer is a polyimide film, the thickness of the layer is between about 200 and about 800 nm.

The sensors of the invention can display hydrogen selectivity in a mixture of gases, where the gas mixture includes a plurality of gases to which the sensor is sensitive. In an embodiment, the gas mixture includes CO. In an embodiment, the sensors of the invention display hydrogen selectivity in gas mixtures containing hydrogen, carbon containing gases and unvarying amounts of oxygen.

The sensors of the invention are also capable of selectively detecting hydrogen dissolved in a liquid. For example, the sensors of the invention are capable of detecting hydrogen dissolved in oil or a solvent. In an embodiment, the sensors of the invention can display reduced baseline drift in a liquid environment as compared to a sensor without a hydrogen selective coating in the same environment. In an embodiment, the sensors of the invention display reduced baseline drift in an oil environment.

In an embodiment, the invention provides a hydrogen sensor comprising a MIS sensor and a layer of hydrogen selective material attached to the top surface of the layer of catalytic metal of the MIS sensor. The hydrogen selectivity of the sensors of the invention is improved compared to that of MIS sensors not coated with a hydrogen selective material. In an embodiment, the MIS sensor is capacitance-based.

BRIEF DESCRIPTION OF THE FIGURES

FIG. 3A: Top view of layout of the MIS sensor after polyimide (PI) coating: each device contains four identical quarter-circle shaped sensors, with bonding pads on the corners;

FIG. 3B: Side view of layout of the MIS sensor after polyimide (PI) coating (not to scale).

DETAILED DESCRIPTION OF THE INVENTION

Figure 1:
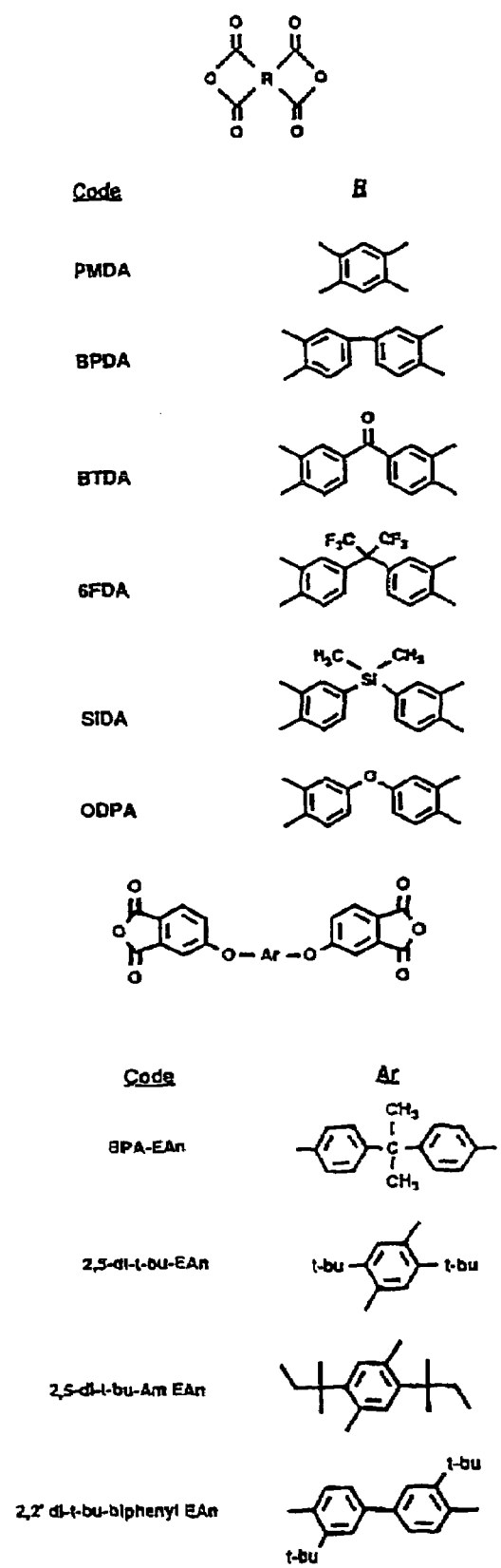
FIG. 1: Common dianhydride structures.

The present invention provides a gas sensor having improved hydrogen selectivity. As used herein, hydrogen selectivity indicates preferential response to hydrogen. For a hydrogen selective sensor, changes in sensor output due to changes in hydrogen concentration are larger than changes in sensor output due to equivalent concentration changes of other gases. The extent to which a sensor preferentially responds to hydrogen in a gas mixture can be determined by the extent to which the sensor voltage shift is due to hydrogen. In the ideal limit, a hydrogen selective sensor responds only to hydrogen and is not affected by other gases. The sensors of the invention can display hydrogen selectivity in a mixture of gases, where the gas mixture includes a plurality of gases to which the unmodified sensor is sensitive. The sensors of the invention may display hydrogen selectivity in some gas mixtures, but not in others. In an embodiment, the gas mixture includes CO. In an embodiment, the sensors of the invention display hydrogen selectivity in gas mixtures containing hydrogen, hydrocarbon gases capable of dissociating in the presence of the catalytic metal to form hydrogem and unvarying amounts of oxygen. In another embodiment, the sensors of the invention display hydrogen selectivity in a gas mixture comprising hydrogen and at least one gas selected from the group consisting of methane, ethylene, acetylene, carbon monoxide, and oxygen (where the oxygen content of the gas mixture does not vary by greater than 10%).

In general, MIS sensors comprise a semiconductor substrate, a thin layer of insulator material attached to the top surface of the substrate, and a layer of catalytic metal attached to the top surface of the layer of insulator material. The bottom surface of the semiconductor substrate may be metallized and contacts may be attached to the layer of catalytic metal. As referred to herein, the top surface of the substrate is the surface on which the insulator is fabricated. During typical fabrication processes, this surface is typically uppermost. When the sensor is in use, the sensor may be positioned so that the layers of insulator material, catalytic material and hydrogen selective material are not above the substrate (e.g. the sensor may be inverted in use).

Useful catalytic metals for MIS sensors include palladium, platinum, and iridium. Alloys of these metals, such as palladium-silver alloys, are also useful in the practice of the invention. In an embodiment, the catalytic metal is palladium. Typical thicknesses of the metal layer are between about 20 nm and about 2000 nm.

Any insulator material known to the art can be used for the insulator layer. In an embodiment, the insulator material is silicon dioxide. The typical thickness of the insulating layer is less than about 100 nm.

Any semiconducting material known to the art can be used for the semiconducting substrate. In an embodiment the semiconducting substrate is silicon. The silicon may be either n doped or p doped Further details of the construction of MIS sensors are known to those skilled in the art. Hughes et al. (Hughes, R. C., R. Bastasz, and W. P. Ellis, *Hydrogen Sensing in Vacuum Systems with Catalytic Field Plate Mnos Capacitors.* Applied Surface Science, 1997. 115(1): p. 74-79), Lundstrom (Lundstrom, I., *Why Bother About Gas-Sensitive Field-Effect Devices?* Sens. Actuators A, 1996. 56:

p. 75-82; Lundstrom, I., *Hydrogen Sensitive Mos-Structures: 1. Principles and Applications*. Sens. Actuators, 1981. 1: p. 403-426), and Lundstrom and Soderberg (Lundstrom, I. and D. Soderberg, *Hydrogen Sensitive Mos-Structures: 2. Characterization*. Sens. Actuators, 1981. 2: p. 105-138) hereby incorporated by reference, provide examples of MIS sensor configurations.

As used herein, a hydrogen selective material has a selectivity greater than one for hydrogen over at least one other gas of interest that the uncoated MIS sensor may also be sensitive to. These gases, include, but are not limited to methane ($CH_4$), ethylene ($C_2H_4$), acetylene ($C_2H_2$), and CO. In the present invention, the hydrogen selective material is selected so that it has a high selectivity for hydrogen compared to the other gas (or gases) of interest. Transport of gases through a membrane can be described by several parameters. As used herein, the flux, $J_i$, through a membrane is the number of moles of a specified component i passing per unit time through a unit of membrane surface area normal to the thickness direction. The permeance or pressure normalized flux, $P_i$, is the flux of component i per unit transmembrane driving force. For a diffusion process, the transmembrane driving force is the gradient in chemical potential for the component (Kärger, J. Ruthven, D. M., Diffusion in Zeolites, John Wiley and Sons: New York, 1992, pp. 9-10). The ideal selectivity of a membrane for components i over j, $S_{i/j}$ is the permeability of component i divided by the permeability of component j. $S_{i/j}$ can also be called the permselectivity The ideal selectivity is the ratio of the permeabilities obtained from single gas permeation experiments. The actual selectivity (also called separation selectivity) for a gas mixture may differ from the ideal selectivity. In different embodiments, the selectivity is greater than about 25, greater than about 50, greater than about 75 or greater than about 100.

The selectivity of a membrane for one component over another is often measured by applying a pressure differential across the membrane. For a polymer film the ideal selectivity of the film for one gas over another can depend on the pressure differential, since the pressure differential can influence the solubilities of the gases in the polymer. In the practice of the present invention, a large pressure gradient may not exist across the hydrogen selective layer. Therefore, the ideal selectivity for hydrogen over another gas as determined from permeability measurements conducted under a pressure gradient may not directly correspond to the actual selectivity under the environmental conditions experienced by the sensor. In an embodiment, the ideal selectivity of the hydrogen selective layer material for hydrogen over another gas as determined from permeability measurements conducted under a pressure gradient is greater than about 25, greater than about 50, greater than about 75, or greater than about 100.

Figure 2:
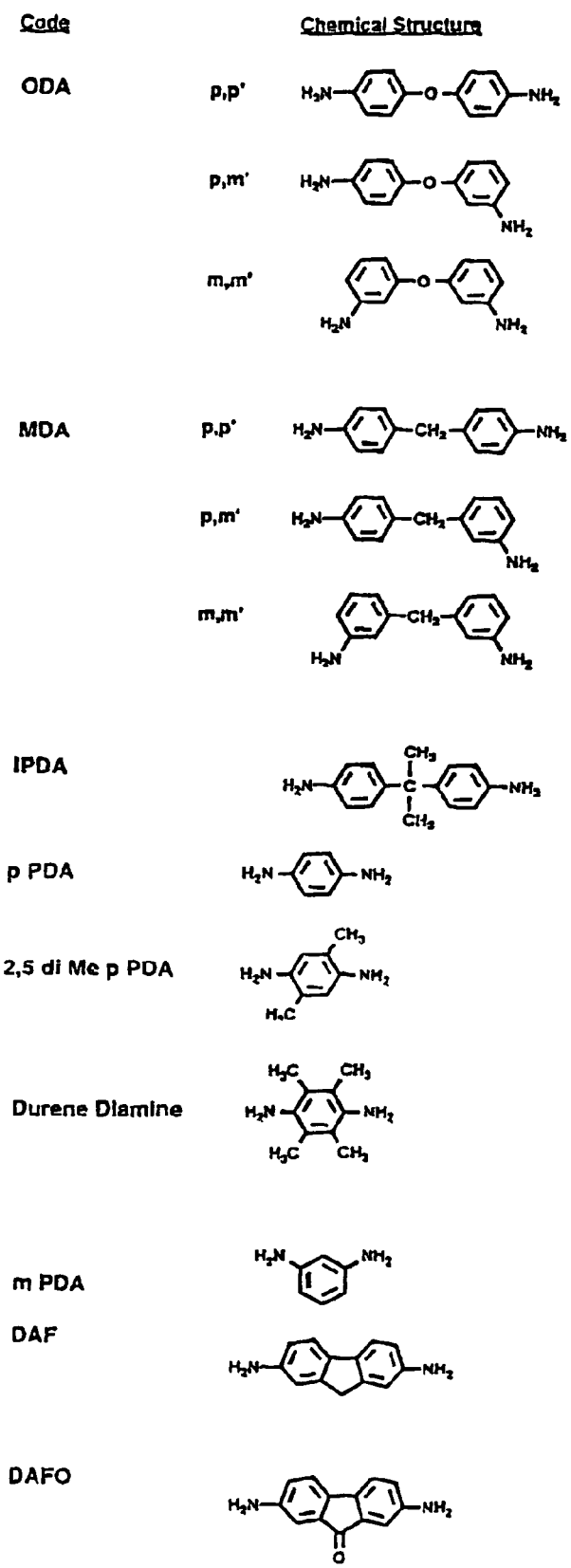
FIG. 2: Common diamine structures.
Figure 2:
Figure 2:
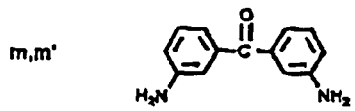
Figure 2:
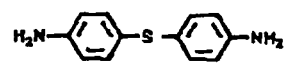
Figure 2:
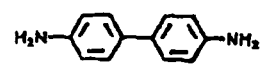
Figure 2:
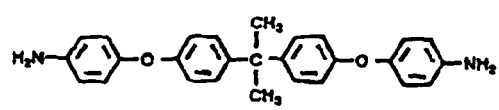
Figure 2:
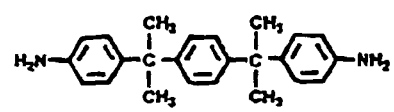
Figure 2:
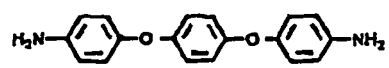
Figure 2:
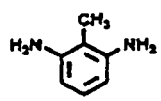
Figure 2:
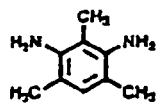
Figure 2:
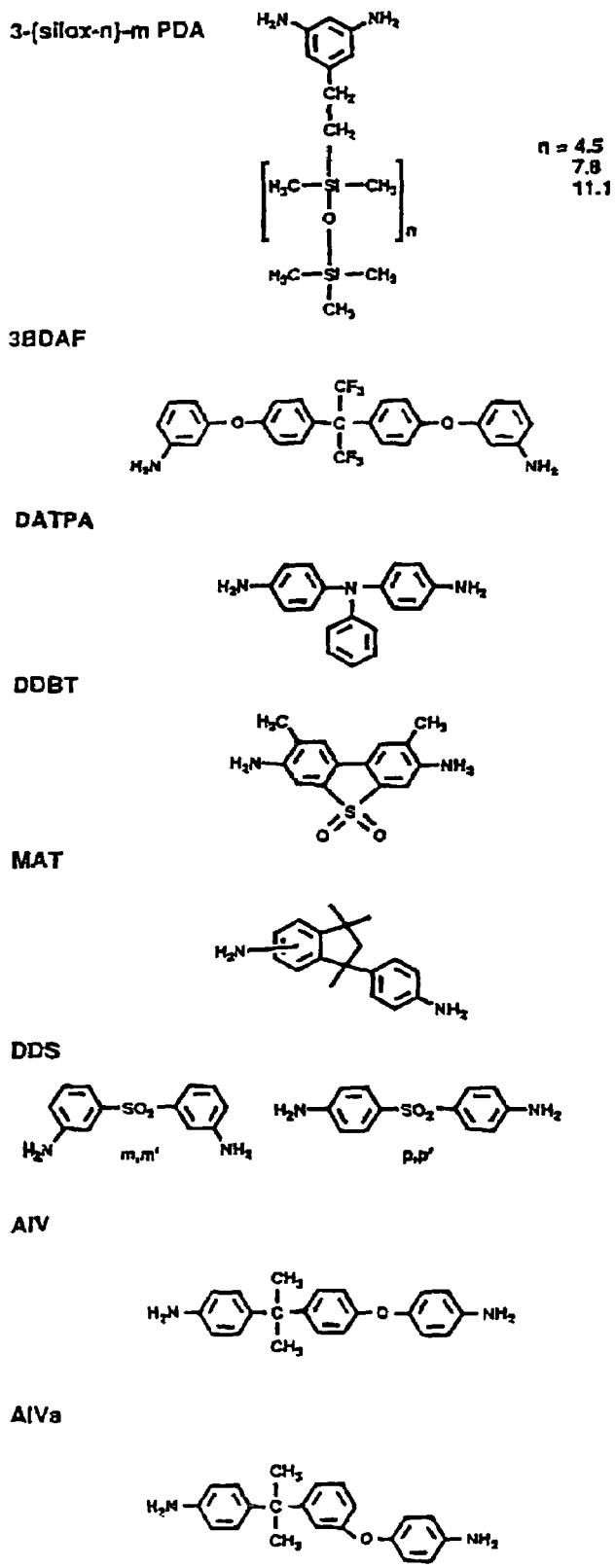
Figure 2:
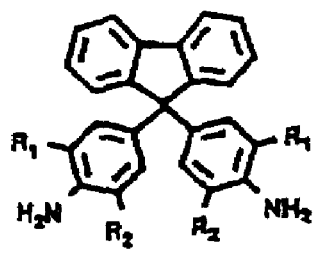
Figure 2:
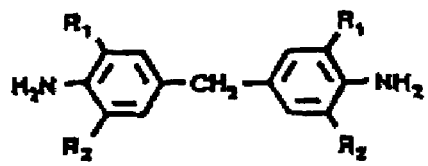

In an embodiment, the hydrogen selective material is selected so that it has a high $H_2/CO$ selectivity. In different embodiments, the ideal $H_2/CO$ selectivity is greater than 50 or greater than 75. These ideal selectivity values may be those determined from permeability measurements conducted under a pressure gradient. Although CO itself is generally not detected by MIS devices, it can still affect response to $H_2$ and other gases through strong competitive adsorption on the Pd surface. For example, the rate of response of uncoated MIS devices to $H_2$ is known to be dramatically slowed by the presence of even ppm levels of CO because of strong adsorption (poisoning) by CO (M. Eriksson, L.-G. Ekedahl, The influence of CO on the response of hydrogen sensitive Pd-MOS devices, Sens. Actuators B 42 (1997) 217.; M. Eriksson, L.-G. Ekedahl, Real time measurements of hydrogen desorption and absorption during CO exposures of Pd: hydrogen sticking and dissolution, Appl. Surf. Sci. 133 (1998) 89.) As shown in Table 1 (Baker, R., *Membrane Technology and Applications*. 2000: New York: McGraw-Hill ), several polymeric membranes used for hydrogen separation have $H_2/CO$ selectivities in excess of 25. Ideal selectivities for various polyimides can also be calculated and are shown in Table 2 (Table 2 also presents relevant references; permeability data used to calculate Table 2 is also presented in Ghosh, M. K. and K. L. Mittal, *Polyimides, Fundamentals and Applications*. Polyimides for Gas Separation, ed. M. Langsam. 1996, New York: Marcel Dekker, Inc. 197). The polyimides in Table 2 are classified by their diamine and dianhydride portions. FIG. 1 illustrates common dianhydride structures and FIG. 2 illustrates common diamine structures (Ghosh, M. K. and K. L. Mittal, *Polyimides, Fundamentals and Applications*. Polyimides for Gas Separation, ed. M. Langsam. 1996, New York: Marcel Dekker, Inc.). In an embodiment, the permeability of the hydrogen selective material to CO is nonzero.

In an embodiment, the hydrogen selective material is selected so to have good hydrogen selectivity over methane ($CH_4$), ethylene ($C_2H_4$), acetylene ($C_2H_2$) and other light hydrocarbons. As used herein, a light hydrocarbon is a hydrocarbon that is a vapor a temperatures less than or equal to 100° C. In different embodiments, the permselectivity of $H_2$ over light hydrocarbons is greater than 75 or greater than 100. The permselectivity of $H_2$ over small hydrocarbons is greater than 100 for most polyimide materials (K. Tanaka, H. Kita, M. Okano, K. Okamoto, Permeability, permselectivity of gases in fluorinated and non-fluorinated polyimides, Polymer 33 (1992) 585). In an embodiment, the permeability of the hydrogen selective material to small hydrocarbons is nonzero.

In an embodiment, the hydrogen selective material is selected to have good hydrogen selectivity over nitrogen. In an embodiment, $H_2/N_2$ selectivity is greater than 100 (Table 1). In an embodiment, the permeability of the hydrogen selective material to nitrogen is nonzero.

In an embodiment, the hydrogen selective material need not be highly permselective over oxygen. In an embodiment, the response time of the sensor is improved when oxygen is allowed to pass through the hydrogen selective layer. In an embodiment, the oxygen concentration in the environment does not vary substantially during the measurement. In different embodiments, the change in oxygen concentration is less than 5% or less than 10%.

In an embodiment, the hydrogen selective material is a polymeric material with no substantial through-porosity. Polymeric layers can be formed by any method known to the art, including spin coating. Polyimide membranes can also be formed from multilayer electrolyte films (Sullivan, D. M. and Bruening, M. L., Ultrathin, Gas-Selective Polyimide Membranes Prepared from Multilayer Polyelectrolyte Films, Chem. Mater. (2003), 15, 281-287). The hydrogen selective material may be, but is not required to be, a commercial material. In an embodiment, the hydrogen selective material is not a cross-linking negative photoresist based on a synthetic polyisoprene and containing a bisazid photoinitiator or a positive photoresist containing diazonapthoquinone dispersed in an alkali-soluble resin and containing diazonium, carbonyl, sulphonyl and hydroxyl groups in a polymeric-benzene ring-structure (Hedborg et al., Polymer membranes for modification of the selectivity of field-effect gas sensors, Sensors and Actuators B, 7 (1992), 661-664).

In an embodiment, the hydrogen selective material is a polyimide material. The polyimide material may be any polyimide polymer or material comprising a polyimide polymer known to the art. Polyimides are typically made by polymerization of dianhydrides and diamines or their derivatives. The polyimide material can also be formed from a mixture of diamines. The polyimide material can also be a mixed matrix material, a composite material incorporating a non-polyimide polyimide material into a polyimide matrix. Mixed matrix polyimides containing metal and metal oxides (Sawada, T. and Ando, S., Synthesis, Characterization, and Optical Properties of Metal-Containing Fluorinated Polyimide Films, Chem. Mater. (1998), 10, 3368-3378) and aluminophosphates (Jeong, H. K. et al., Fabrication of Polymer/Selective-Flake Nanocomposite Membranes and Their Use in Gas Separation, Chem. Mater. (2003), 16, 3838-3845) have been reported.

Typically, polyimide materials are synthesized via a two-step process. The first step involves reacting a dianhydride and a diamine to form a polyamic acid (PAA) precursor. The PAA precursor is subsequently converted to a polyimide via thermal, chemical or solution imidization. In addition, the polyimide material can be a film formed by imidization of poly(amic acid)/PAH membranes (Sullivan, D. M. and Bruening, M. L., Ultrathin, Gas-Selective Polyimide Membranes Prepared from Multilayer Polyelectrolyte Films, Chem. Mater. (2003), 15, 281-287).

In an embodiment, the polyimide is polyimide (PI) Pyralin® PI-2555 (a reaction product of benzophenone tetracarboxylic dianhydride 4,4-oxydianiline m-phenylene diamine, BTDA-ODA-MPD; purchased from DuPont HD Microsystems™. This material has a cure temperature of 295° C. and a glass transition temperature of 325° C. This material, when formed as a layer on top of a palladium layer on a MIS sensor, has led to improved hydrogen selectivity of the MIS-based sensor, as described in Example 2. In particular, the sensor described in Example 2 was selective to hydrogen in gas mixtures containing $C_2H_2$, $C_2H_4$, $C_2H_6$, $CH_4$, CO and Ar. However, any material which leads to improved MIS-based sensor hydrogen selectivity is suitable for use with the invention.

Without wishing to be bound by any particular belief, it is believed that materials which are sufficiently structurally similar to PI-2555 will also lead to improved MIS-based sensor hydrogen selectivity. These materials are expected to include other polyimides as well as polyetherimides. Materials similar in structure to PI-2555 are expected to include polyimide materials formed by reacting BTDA with p,p' ODA, p,m' ODA, m,m' ODA and combinations of these diamines. Useful polyimide materials can also be formed by reacting BTDA with a combination of diamines selected from the group consisting of combinations of p,m' ODA or m,m' ODA with MDA (equivalent to m PDA in FIG. 2) and combinations of p,p' ODA, p,m' ODA, or m,m' ODA with p PDA.

In one embodiment, the polymeric material is formed by polymerization of BTDA with a diamine selected from the group consisting of p,p' ODA, p,m' ODA, m,m' ODA and combinations thereof. In another embodiment, the polymeric material is formed by polymerization of BTDA with a first diamine selected from the group consisting of p,p' ODA, p,m' ODA, and m,m' ODA and a second diamine selected from the group consisting of p PDA and m PDA.

In an embodiment, the polyimide is selected to have a high predicted $H_2/CO$ selectivity. Polyimides having predicted ideal $H_2/CO$ selectivities greater than 50 include polyimides based on PDMA (pyromellitic dianhydride) and p,m'ODA (oxydianiline), polyimides based on BPDA (biphenyltetracarboxylic dianhydride) and p,p' ODA or p,p' methylene dianiline (p,p' MDA) or p,p' diaminophenyl sulfone (DDS) or 3,7-diamino-2,8-dimethyl-dibenzothiophene-5,5-dioxide (DDBT), polyimides based on BTDA and p,p' ODA or BAPHF and polyimides based on 6FDA and p,m' ODA, m,m' ODA, or m-PDA(see Table 2).

In an embodiment, the hydrogen selective material is a polyimide material formed by reacting PDMA (pyromellitic dianhydride) and p,m' ODA (oxydianiline), BPDA (biphenyltetracarboxylic dianhydride) and p,p' ODA or BTDA and p,p' ODA.

Appropriate molar ratios of dianhydride to diamine are known to those skilled in the art. As used herein, a polymeric or polyimide material may also contain other components such as adhesion promoters known to those skilled in the art.

The hydrogen selective material may also be an inorganic material. Two papers in this field have demonstrated that silica membranes can have $H_2/CO$ selectivity as high as 119-125, depending on operating temperature (Dong-wook Lee et al. *Preparation and characterization of $SiO_2$ composite membranes for purification of hydrogen for PEMFC.* Industrial and Engineering Chemistry Research. Vol. 41 (2002), 3594-3600; Dong-wook Lee et al. Preparation and characterization of $SiO_2$ composite membrane for purification of hydrogen from methanol steam reforming as an energy carrier system for PEMFC. Separation and purification technology, 32 (2003), 45-50).

It is expected that the signal from the sensor due to hydrogen will depend upon the thickness of the hydrogen selective layer. The thickness of the hydrogen-selective layer can affect the sensor output level, with thicker layers leading to decreased sensor output. The thickness of the hydrogen-selective layer is selected so that a reasonable signal level is obtained. In an embodiment, the signal level is greater than about 10 mV. When the sensor is exposed to a gas which causes a voltage shift, the changes in voltage will typically take place gradually rather than instantaneously. The response time can be defined as the time for the voltage shift to reach a certain percentage (e.g. 90%) of its ultimate value. The thickness of the hydrogen selective layer is selected so that a reasonable response time is achieved. The response time is expected to scale with the thickness of the layer squared. In different embodiments, the response time is less than about 30 minutes, less than about 10 minutes, and less than about 5 minutes. However, the hydrogen selective layer should be thick enough so that hydrogen selectivity of the sensor is observed. In an embodiment, the selective layer is thick enough that any defects in the layer do not dominate mass transfer through the coating. In different embodiment where the hydrogen selective layer is a polyimide film, the thickness of the layer is greater than 200 nm, between 200 and 1000 nm and between 200 and 800 nm.

$H_2$ selectivity in the sensors of the invention can be obtained without complete blockage of contaminant gases from accessing the Pd surface. The hydrogen selective layer still allows small gases to pass through the membrane; these gases simply diffuse at a substantially slower rate than $H_2$. It is useful to consider the effect of the hydrogen selective layer on two types of gases, those that can react at the metal surface versus those that do not. For non-reactive gases, the rate of diffusion across the hydrogen selective should have no effect on the steady-state gas concentrations at the metal surface; the concentration of non-reactive gases at the hydrogen selective layer-metal interface will therefore achieve a value that is in equilibrium with the gas phase.

Whereas non-reactive gases will accumulate at an equilibrium concentration along the hydrogen selective layer-metal interface, that is not necessarily the case for gases that can react on the catalytic metal surface, such as $C_2H_2$, $C_2H_4$, and (in the presence of oxygen) CO. These gases can undergo decomposition, hydrogenation, or oxidation at the catalytic metal surface, thus, providing a continuous "sink" that removes these reactive gases from the permeate side of the hydrogen selective layer. A gradient in chemical potential can therefore be established that allows the permselective properties of the hydrogen selective layer to be exploited. For hydrogen selective layers which are sufficiently thick slow diffusion of reactive contaminant gases across the layer can limit their effect on the sensor response.

Without wishing to be bound by any particular belief, the modified properties of the metal-hydrogen selective layer may also affect the response of the sensors of the invention. Chemical and/or physical attachment between a polymer film and metal surface (F. Iacona, M. Garilli, G. Marletta, O. Puglisi, S. Pignataro, Interfacial reactions in polyimide metal systems, J. Mater. Res. 6 (1991) 861) can have (at least) one of two effects: (1) Contacts between the polymer and the surface can break up the surface into relatively small ensembles of metal atoms that are open for adsorption of analytes. Ensemble size effects are well-known to be operable for adsorption of CO and unsaturated hydrocarbons; CO prefers to adsorb in three-fold or four-fold hollow sites above open metal terraces (J. R. Monnier, J. W. Medlin, Y.-J. Kuo, Selective isomerization of 2,5- dihydrofuran to 2,3- dihydrofuran using CO-modified, supported Pd catalysts, Appl. Catal. A 194-195 (2000) 463; V. V. Kaichev, 1. P. Prosvirin, V. I. Bukhtiyarov, H. Unterhalt, G. Rupprecher, H. J. Freund, High-pressure pressure studies of CO adsorption on Pd(1 1 1) by X-ray photoelectron spectroscopy and sum-frequency generation, J. Phys. Chem. B 107 (2003) 3522; M. K. Rose, T. Mitsui, J. Dunphy, A. Borg, D. F. Ogletree, M. Salmeron, P. Sautet, Ordered structures of CO on Pd(1 1 1) studied by STM, Surf. Sci. 512 (2002) 48) and olefins, such as ethylene and acetylene generally require a minimum of two to three adjacent vacant surface atoms (J. W. Medlin, M. A. Allendorf, A theoretical study of the adsorption of acetylene on the (1 1 1) surfaces of Pd, Pt, Ni, and Rh, J. Phys. Chem. B 107 (2003) 217; D. Stacchiola, I. Burkholder, W. T. Tysoe, Ethylene adsorption on Pd (1 1 1) studied using infrared reflection-absorption spectroscopy, Surf. Sci. 511 (2002) 215; R. M. Watwe, R. D. Cortright, M. Mavrikakis, J. K. Norskov, J. A. Dumesic, Density functional theory studies of the adsorption of ethylene and oxygen on Pt(1 1 1) and Pt3Sn(1 1 1), J. Chem. Phys. 114 (2001)) 4663). If $H_2$ sorption can be accomplished by a single free metal atom, the breaking up of the surface into small ensembles could improve $H_2$ selectivity. (2) Polymer-metal interface sites may favor $H_2$ adsorption over adsorption of other gases. A few investigators have previously studied the modification of MIS devices with top-layer polymer and metal oxide films (E. Hedborg, F. Winquist, I. Lundstrom, L. I. Andersson, K. Mosbach, Some studies of molecularly-imprinted polymer membranes in combination with field-effect devices, Sens. Actuators A 37-38 (1993) 796; A. E. Abom, E. Comini, G. Sberveglieri, L. Hultman, M. Eriksson, Thin oxide films as surface modifiers of MIS field effect gas sensors, Sens. Actuators B 85 (2002) 109). It has been shown that such devices have unique sensitivity for particular gases, such as $NH_3$, at these modified sites. These high sensitivities have been attributed to the unique properties of interfacial sites (e.g., for $NH_3$ dissociation).

The invention also provides a method for improving the hydrogen selectivity of a MIS hydrogen sensor comprising the steps of:

providing a MIS sensor comprising a semiconductor substrate, a layer of insulator material attached to the substrate, a layer of catalytic metal attached to the layer of insulator material; and coating the layer of catalytic metal with a hydrogen selective material.

The invention further provides a method for making a hydrogen selective metal-insulator-semiconductor (MIS) hydrogen sensor comprising the steps of:

providing a MIS sensor comprising a semiconductor substrate, a layer of insulator material attached to the substrate, a layer of catalytic metal attached to the layer of insulator material; and coating the layer of catalytic metal with a layer of hydrogen selective material wherein the layer of hydrogen selective material comprises a polymeric material and is between 200 nm and 1000 nm thick.

The invention also provides methods for detecting hydrogen in a mixture of gases. In an embodiment, the method comprises the steps of:

providing a metal-insulator-semiconductor (MIS) sensor responsive to hydrogen, the sensor comprising a semiconductor substrate, a layer of insulator material attached to the substrate, a layer of catalytic metal attached to the layer of insulator material, and a layer of hydrogen selective material attached to the layer of catalytic material, wherein the layer of hydrogen selective material comprises a polymeric material and is between 200 nm and 1000 nm thick;

exposing the hydrogen sensor to an environment comprising a gas mixture, wherein the gas mixture comprises hydrogen and a second gas selected from the group consisting of hydrogen containing gases capable of dissociating to form hydrogen and gases which can affect the response of the catalytic metal to hydrogen, wherein during exposure of the sensor to the environment the oxygen content of the gas mixture does not vary by greater than 10% ; and detecting the response of the hydrogen sensor to the environment, thereby detecting hydrogen in the gas mixture.

The MIS sensor is responsive to hydrogen such that the presence of gas-phase $H_2$ at the catalytic metal/hydrogen selective layer interface results in either a voltage shift in the capacitance-voltage (C-V) curve of a capacitor, or in the current-voltage characteristic of a diode or transistor, depending on the configuration of the sensor. The response of the sensor to the environment which comprises a gas mixture is detected by measuring the relevant voltage shift. In the practice of the invention, the sensor is matched to the environment so that the response of the sensor to the environment is due primarily to the hydrogen present in the environment. The sensor is matched to the environment by considering the gases other than hydrogen which are expected to be present in the environment and which are expected to vary in concentration and selecting the hydrogen selective material to be highly selective for hydrogen over these gases.

The hydrogen sensor may be exposed to the environment by placing the sensor in a gaseous environment or by placing the sensor in a liquid environment which comprises a mixture of gases dissolved in the liquid. The liquid may be an oil or a solvent. Suitable oils for the practice of the invention include, but are not limited to mineral oil and silicon oil.

Typical environment temperatures are between 20 and 125° C. For hydrogen selective polymeric films, these expected use temperatures are below the glass transition temperature of the polymer.

The sensors of the invention can also be used for detecting hydrogen in an environment which does not contain other gases that the uncoated sensor would be sensitive to. In these methods of detecting hydrogen, a sensor of the invention is provided, the sensor is exposed to the environment, and the response of the sensor to the environment is detected. These methods can be useful where the hydrogen selective coating also reduces the baseline drift of the sensor, as in a liquid environment.

TABLE 1

Selectivities of different hydrogen separation membranes

| | Selectivity | | | Hydrogen pressure-normalized flux $10^{-6}$ $cm^3$ (STP)/ ($cm^2 \cdot s \cdot$ cmHg | Commercial available forms and min. size |
|---|---|---|---|---|---|
| | $H_2/CO$ | $H_2/CH_4$ | $H_2/N_2$ | | |
| Polyaramide (Medal) | 100 | >200 | >200 | — | Hollow fiber 1" * 12" module |
| Polysulfone (Permea) | 40 | 80 | 80 | 100 | Hollow module 1" * 12" module |
| Cellulose Acetate (Separex) | 30-40 | 60-80 | 60-80 | 200 | |
| Polyimide (Ube) | 50 | 100-200 | 100-200 | 80-200 | |

TABLE 2

$H_2/CO$ selectivity for different polyimides

| | $H_2/CO$ selectivity | Ref. |
|---|---|---|
| Polyimides based on PMDA and different diamines Diamine | | |
| p,p' ODA | 39 | [1] |
| p,m' ODA | 68 | [1] |
| BAPHF | 23 | [1] |
| BATPHF | 24 | [1] |
| Polyimides based on BPDA and different diamines Diamine | | |
| p,p' ODA | 79 | [2] |
| | 102 | [1], [3] |
| p,p' MDA | 54 | [2] |
| | 65 | [3] |
| p,p' DDS | 61 | [2] |
| | 66 | [3] |
| DDBT | 55 | [2] |
| BAHF | 27 | [1] |
| BAPHF | 43 | [1] |
| DATPA | 39 | [3] |
| Mesitylene diamine | 16 | [4] |
| Polyimides based on BTDA and different diamines Diamine | | |
| p,p' ODA | 96 | [1], [3] |

TABLE 2-continued $H_2/CO$ selectivity for different polyimides

| | $H_2/CO$ selectivity | Ref. |
|---|---|---|
| BAHF | 44 | [1] |
| BAPHF | 51 | [1] |
| BATPHF | 45 | [1] |
| DATPA | 23 | [3] |
| Mesitylene diamine | 26 | [4] |
| Polyimides based on 6FDA and different diamines Diamine | | |
| p,p' ODA | 35 | [1], [3] |
| p,m' ODA | 57 | [1] |
| m,m' ODA | 424 | [5] |
| BAHF | 26 | [1] |
| APAP | 49 | [1] |
| BATPHF | 30 | [1] |
| p-PDA | 40 | [5] |
| m-PDA | 57 | [4] |
| 2,6 TDA | 34 | [4] |
| Mesitylene diamine | 11 | [4] |
| 2,5 DiM p PDA | 32 | [3] |
| durene diamine | 1 | [4] |
| DATPA | 29 | [3] |
| Polyimides based on ODPA and different diamines) | | |
| DATPA | 52 | [3] |

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods other than those specifically exemplified can be employed in the practice of the invention without resort to undue experimentation. All art-known functional equivalents of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention All references cited herein are hereby incorporated by reference to the extent that there is no inconsistency with the disclosure of this specification. Some references provided herein are incorporated by reference herein to provide details concerning MIS sensor fabrication and additional polymeric compositions.

EXAMPLE 1

Mis Device Fabrication

The Compound Semiconductor Research Laboratory (CSRL) at Sandia National Laboratories (New Mexico) prepared the Pd/SiO$_2$/n-Si capacitors used for this work. These capacitors were fabricated in a similar manner as described in previous publications, which yielded a similar overall device structure R. C. Hughes, R. Bastasz, W. P. Ellis, Hydrogen sensing in vacuum systems with catalytic field plate MNOS capacitors, Appl. Surf. Sci. 115 (1997) 74. A 50 nm Pd film was deposited by electron-beam evaporation on a 50 nm layer of SiO$_2$ prepared by thermal oxidation of the Si wafer. Auger electron spectroscopy depth profiling was applied to analyze samples from each production batch to verify film composition.

A spin-coating technique was applied to add an attached layer of polyimide (PI)-2555 (a reaction product of benzophenone tetracarboxylic dianhydride 4,4-oxydianiline m-phenylene diamine, BTDA-ODA-MPD; purchased from DuPont HD Microsystems™) to the top of the Pd surface. The PI-2555 was coated onto the palladium surface using a spin coater from Specialty Coating Systems Inc., Model P6708. Spin speeds of 1000, 4000 and 6000 rpm were used to obtain different coating thicknesses. The coated sensors were baked at 100, 200 and 300° C. in sequence for 2, 30 and 30 min, respectively. The cured coating layer thickness was measured using ellipsometry (Ellipsometer from Modified J. A. Woollam; Stereoscope: Leica Model MZ6). Unless otherwise noted, experiments on coated sensors were carried out on coatings of measured thickness 670 nm. Atomic force microscopy indicated that the surfaces of both uncoated and coated sensors were smooth to within <±3 nm, indicating that the PI film thickness was highly uniform. A schematic of the spin-coated MIS sensor layout is presented in FIGS. 3A and 3B. FIG. 3A: top view, each device contains four identical quarter-circle shaped sensors (1), with bonding pads (2) on the corners. The length (I) of the assembly is also shown. As fabricated, the length was 4 mm. FIG. 3B: side view showing the bond pad (2), n-doped silicon wafer semiconductor substrate (3), the oxide layer (4), which has bulk and gate portions, the palladium catalytic metal layer (5) and the polyimide coating (6) and the metallized back side (7) (not to scale).

EXAMPLE 2

Sensor Response to Hydrogen, Contaminant Gas and Hydrogen/Contaminant Gas Mixtures Each sensor to be tested was mounted on a sample holder that was inserted in a gas flow cell. Electrical leads for sensor heating were attached to the capacitor base and sensor bond pads. Resistive heating for the mounted sensor was achieved via a conductive button heater (HeatWave Labs Inc.) and the sensor temperature was measured by a thermocouple spot-welded to the heater body. The surface temperature of the sensor has been measured to be within 3° C. of the heater body temperature. The sample holder and flow cell configurations have been discussed in a previous publication (J. W. Medlin, A. H. McDaniel, M. A. Allendorf, R. Bastasz, Effects of competitive CO adsorption on the hydrogen response of MIS sensors: the role of metal film morphology, J. Appl. Phys. 93 (2003) 2267). Shifts in the C-V curve of each capacitor were measured using a program that records the voltage shift required to maintain a constant capacitance value at the point of maximum slope along the C-V curve. Since the sensor response to H$_2$ is a negative-going signal, the addition of H$_2$ shifts the inflection point in the C-V curve to lower bias voltage. The baseline response was zeroed at the start of each experiment due to a baseline drift problem, which is well known for Pd SiO$_2$ Si sensors (I. Robins, Drift effects in transition-metal gate MOS and MISFETs, Sens. Actuators B 15 (1993) 238), causing some variation in H$_2$ response during different experimental runs. Typical drifting rates are approximately 10 mV/h. Except where noted otherwise, tests were performed with the sensor held at 100° C., under atmospheric pressure with a H$_2$ concentration of 500 ppm in the cell gas mixture. A gas mixture (200 ppm C$_2$H$_2$, 400 ppm C$_2$H$_4$, 400 ppm C$_2$H$_6$, 2000 ppm CH$_4$, 3000 ppm CO and balance Ar)) was used to assess sensitivity to small gases other than H$_2$. This mixture is referred to as the "contaminant gas" mixture for convenience. This composition was chosen because it represents typical gases and concentrations present in electrical transformer environments, where MIS sensors are targeted for application. Experiments were optionally performed with 19% O$_2$ (on a volume basis) in the cell to simulate operation in air. All gases were introduced to the flow cell using mass flow controllers. Before conducting each experiment, each sensor was pretreated under synthetic air at 100° C. for at least an hour to drain adsorbed hydrogen from MIS devices, consequently establishing a response base-line. Typically, a much longer pretreatment time (on the order of 12 h) is required for PI-coated sensors due to the additional gas diffusion step through the coating layer. All gases were obtained as research purity (quoted as >99.9%) from Airgas. Argon and/or nitrogen were used as diluents.

Figure 4A:
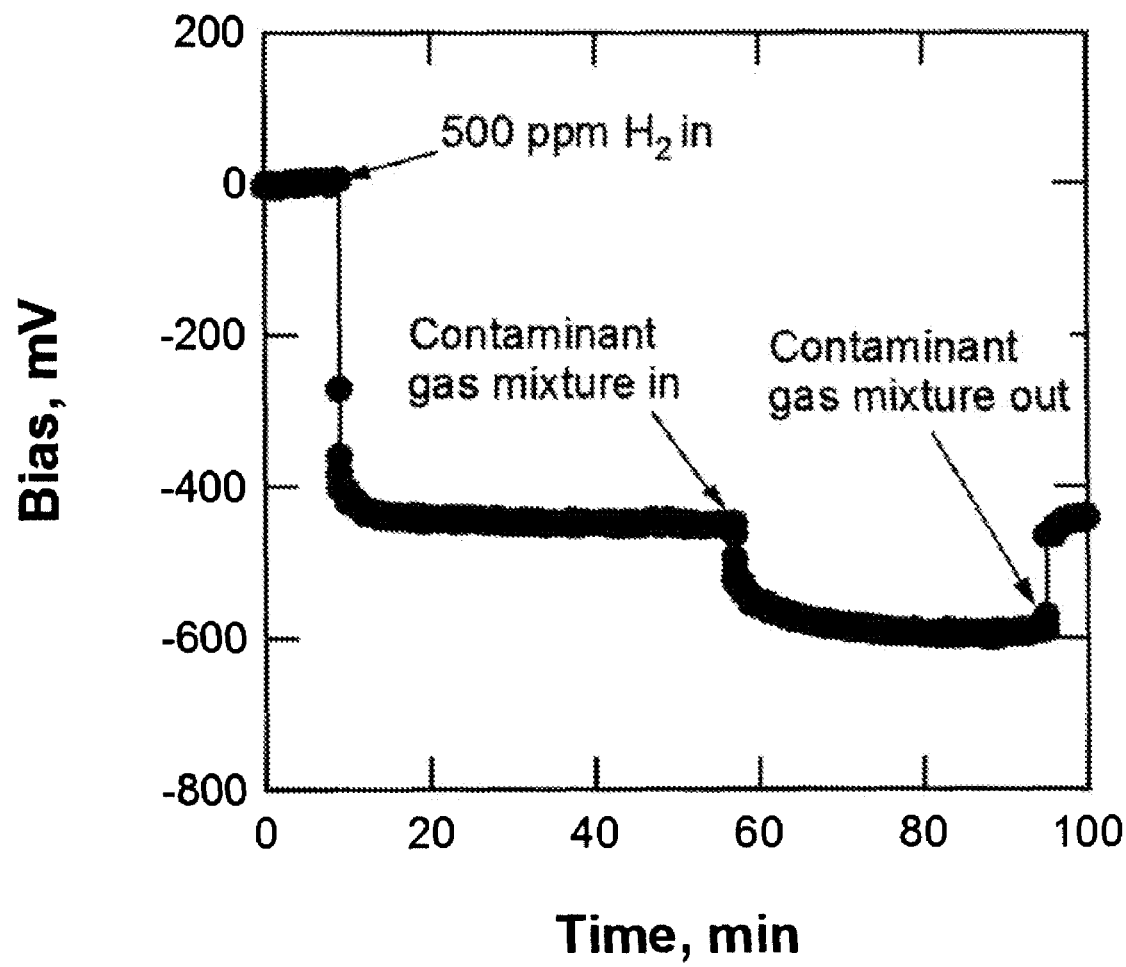
FIG. 4A: Response of uncoated sensors to $H_2$ and the contaminant gas mixture of Example 2 introduced in sequence at the times indicated, in a background of 19% $O_2$ in Ar. Times at which the gas composition was switched are indicated by arrows. Sensors were kept at 100° C. under a pressure of 1 atm.
Figure 4B:
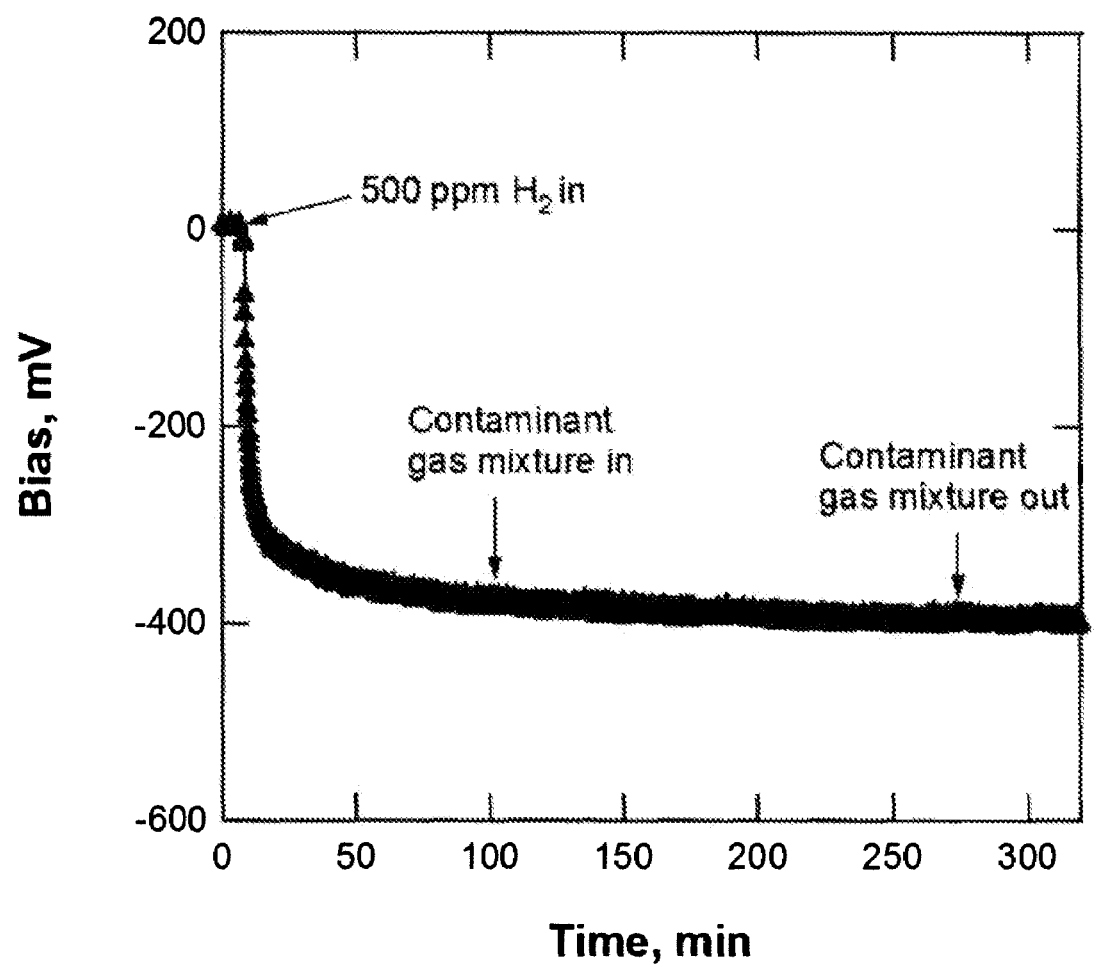
FIG. 4B: Response of coated sensors to $H_2$ and the contaminant gas mixture of Example 2 introduced in sequence at the times indicated, in a background of 19% O2 in Ar. Times at which the gas composition was switched are indicated by arrows. Sensors were kept at 100° C. under a pressure of 1 atm.

To investigate the impact of mixed-gas environments on the MIS response to H$_2$, the performance of both uncoated and coated MIS sensors in H$_2$/contaminant gas mixtures has been studied. Shown in FIG. 4A is the representative response of uncoated sensors to the contaminant gas mixture with H$_2$ in the background. In this set of experiments, H$_2$ was introduced to the flow cell first. A large bias drop was observed almost immediately after the addition of H$_2$ to the flow cell. The contaminant gas mixture mentioned above was then added to the gas stream after the H$_2$ response signal had equilibrated. As shown in FIG. 4A, the addition of contaminant gases to the $H_2$ stream resulted in a substantial increase in the uncoated sensor response (i.e., a decrease in the measured voltage). These results confirmed the cross-sensitivity of uncoated sensors to contaminant gases. Previous investigations have shown that ethylene, acetylene, and CO can each individually affect the sensor response to $H_2$ (J. W. Medlin, A. H. McDaniel, M. A. Allendorf, R. Bastasz, Effects of competitive CO adsorption on the hydrogen response of MIS sensors: the role of metal film morphology, J. Appl. Phys. 93 (2003) 2267; H. Dannetun, I. Lundstrom, L. G. Petersson, Dehydrogenation of acetylene and ethylene studied on clean and oxygen covered palladium surfaces, Surf. Sci. 173 (1986) 148; J. W. Medlin, M. A. Allendorf, A theoretical study of the adsorption of acetylene on the (1 1 1) surfaces of Pd, Pt, Ni, and Rh, J. Phys. Chem. B 107 (2003) 217; A. Borodzinski, A. Golebiowski, Surface heterogeneity of supported Pd catalyst for the hydrogenation of acetylene-ethylene mixtures, Langmuir 13 (1997) 883), so it is not surprising that the response signal is altered significantly by this gas mixture. The cumulative effect produced by the addition of the various gases is a function of complex multicomponent surface chemistry, where both surface reactions (e.g., ethylene dissociation or hydrogenation) and repulsive interactions between adsorbates may be expected to modify response. Using the same operating conditions as those in the uncoated sensor experiments, the response of sensors coated with a 670 nm PI film was not appreciably altered by the addition of contaminant gases (FIG. 4B). Experiments conducted over run times as long as 3 days have confirmed that no effects due to contaminant gas are observed. However, the response time to $H_2$ is slower for the coated device, which could be an important consideration if rapid cycling is needed. This slower response is assumed to be related to the characteristic diffusion time required for $H_2$ to cross the membrane. In any case, the PI coating appears to effectively inhibit the adsorption of contaminant gases at the metal surface, yielding a highly selective $H_2$ sensor.

Figure 5:
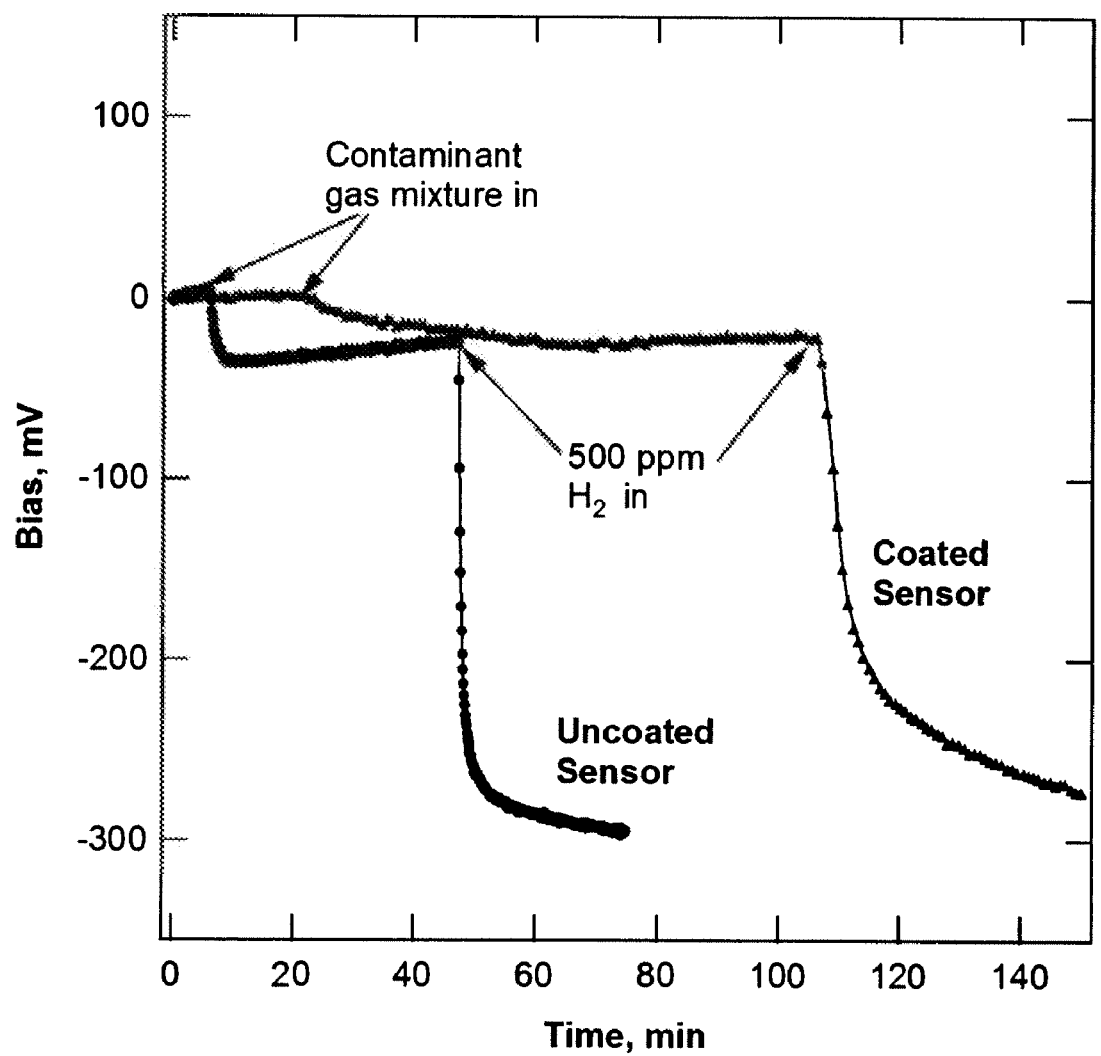
FIG. 5: Response of uncoated and coated sensors to the contaminant gas mixture of Example 2 and $H_2$ introduced in sequence at the times indicated, in a background of 19% $O_2$ in Ar. Times at which the gas composition was switched are indicated by arrows. Sensors were kept at 100° C. under a pressure of 1 atm.

In another comparison between uncoated and coated sensors, the contaminant gas mixture was introduced to the flow cell first after the signal equilibrated in air, but before $H_2$ was added to the flow cell. The goal of these experiments was to investigate whether the uncoated and coated sensors respond to the contaminant gas mixture alone. $H_2$ was added to the stream after the sensor response had equilibrated. Results in FIG. 5 show that both uncoated and coated sensor responses were altered noticeably by the addition of contaminant gases. The response of the coated sensors to the contaminant gas mixture indicates that the "filtering action" of the membrane is not perfect, and that some of the gas components are able to diffuse to the metal surface. The response level of the coated sensor shown in FIG. 5 would correspond to very small levels of $H_2$; for example, bias shifts on the level of 20-30 mV in 10-5 Torr H2 are commonly measured on uncoated devices, even when those devices have not been subjected to any special cleaning procedures. The ability of the contaminant gas mixture to alter response in coated sensor test is not surprising, since non-zero permeabilities are observed for small gases in PI membranes (H. Kita, K. Tanaka, K. Okamoto, Gas permeability and permselectivity in polyimides based on 3,3_, 4,4_-biphenyltetracarboxylic dianhydride, J. Membr. Sci. 47 (1989) 203; K. Tanaka, H. Kita, M. Okano, K. Okamoto, Permeability, permselectivity of gases in fluorinated and non-fluorinated polyimides, Polymer 33 (1992) 585)The contaminant gases will therefore diffuse through the membrane film, albeit at a slower rate relative to $H_2$. Thus, the filtering effect of the PI film with and without $H_2$ in the background observed in the coated sensor test cannot necessarily be explained solely by the permselectivity of the membrane film.

With this sensor, detection down to 10 ppm of $H_2$ was tested; the signal level of the sensor at 10 ppm was in the 200-300 mV range. It is expected that lower concentrations can be detected based on these signal levels.

EXAMPLE 3

Sensor Response to CO and Hydrogen/CO Mixtures

As a further illustration of the effect of contaminant gases on the response of uncoated and coated sensors, experiments were conducted in which CO alone was introduced as a contaminant gas. The effect of CO provides an interesting special case because CO itself is not generally detected by MIS devices; however, it can still affect response to $H_2$ and other gases through strong competitive adsorption on the Pd surface. For example, the rate of response of uncoated MIS devices to $H_2$ is well-known to be dramatically slowed by the presence of even ppm levels of CO because of strong adsorption (poisoning) by CO(M. Eriksson, L.-G. Ekedahl, The influence of CO on the response of hydrogen sensitive Pd-MOS devices, Sens. Actuators B 42 (1997) 217; M. Eriksson, L.-G. Ekedahl, Real time measurements of hydrogen desorption and absorption during CO exposures of Pd: hydrogen sticking and dissolution, Appl. Surf. Sci. 133 (1998) 89). The relative response rates of uncoated MIS devices to $H_2$ in the absence and presence of CO are shown in Table 3. In these experiments, 500 ppm CO was introduced into the flow cell first. After the CO response signal was equilibrated for an hour, $H_2$ was added to the stream. The time for the response change to reach 90% of its steady state value in CO is seen to be >7 min, compared to <15 s for a sensor operating in a CO-free environment. The response rate of PI-coated devices was also measured both in the presence and absence of CO, in a manner similar to that described above. The relative response rates are shown in Table 3. The effect of CO on the dynamic $H_2$ response is clearly much less in the case of the coated sensor, again indicating that access of CO to the catalytic surface has been hindered by the coating. These observations suggest that the coated PI layer does serve as a "filter" of sorts that discourages CO poisoning of the Pd surface. It is also worth mentioning that if $H_2$ is added to the air stream first, no significant CO poisoning effect on the steady-state response was observed for either the coated or uncoated sensors. This finding is in contrast to the results of Medlin et al. (J. W. Medlin, A. H. McDaniel, M. A. Allendorf, R. Bastasz, Effects of competitive CO adsorption on the hydrogen response of MIS sensors: the role of metal film morphology, J. Appl. Phys. 93 (2003) 2267), where CO caused a morphology-dependent change in steady-state sensor response. It is important to point out, however, that the gas compositions are different in Medlin et al. (J. W. Medlin, A. H. McDaniel, M. A. Allendorf, R. Bastasz, Effects of competitive CO adsorption on the hydrogen response of MIS sensors: the role of metal film morphology, J. Appl. Phys. 93 (2003) 2267) versus the current work; in particular, no $O_2$ was present in the studies described in Medlin et al. (ibid.).

TABLE 3

Comparison of the relative $H_2$ response rates of uncoated and coated MIS devices in the absence and presence of 500 ppm CO

| Response time without CO (min) | Response time with CO (min) |
|---|---|
| Uncoated sensor <0.25 | >7 |
| Coated sensor <5 | <5 |

(Response time = time to reach 90% of total bias drop after exposing sensor)

EXAMPLE 4

$O_2$ Effect on Uncoated and Coated Sensors

Figure 6:
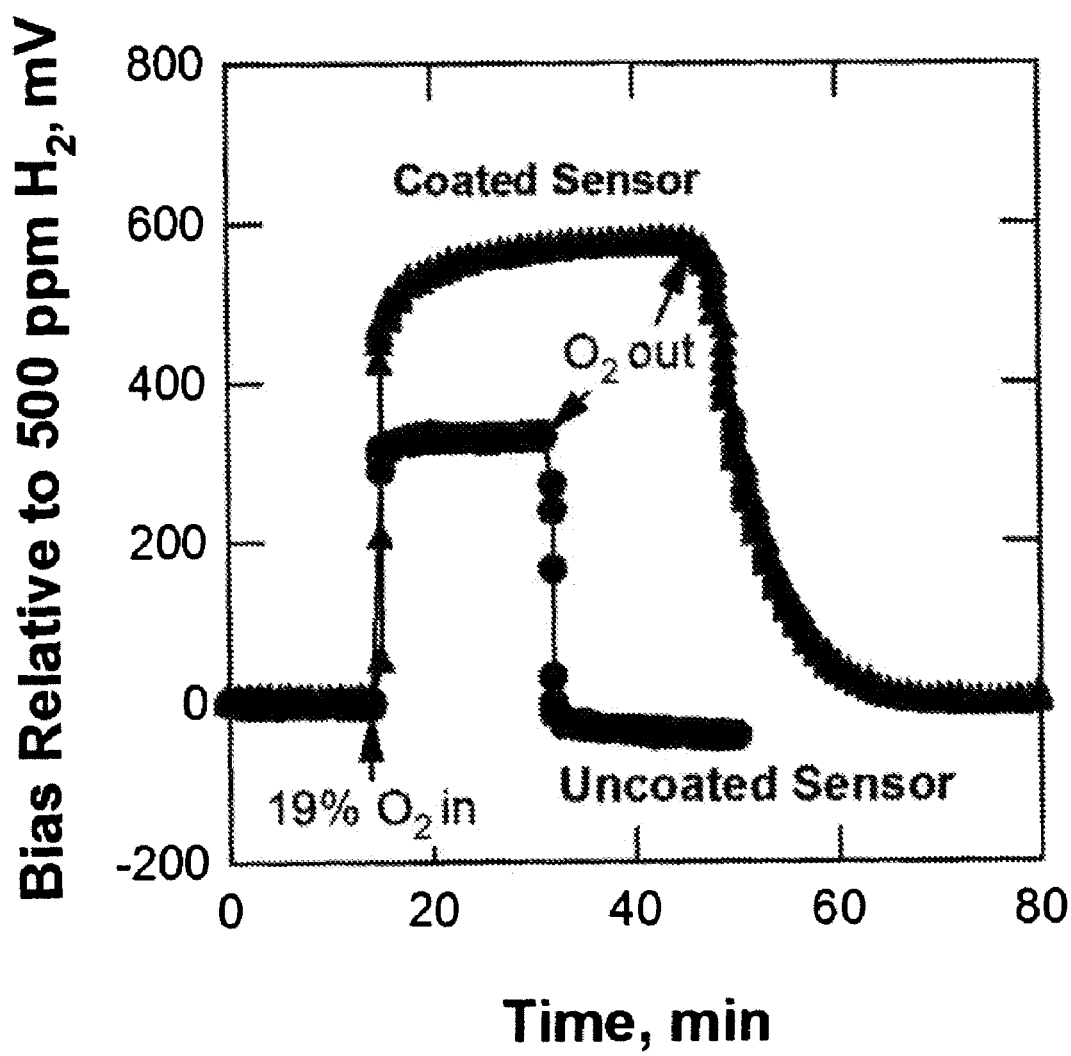
FIG. 6: Response change of uncoated and coated sensors after addition and removal of 19% $O_2$ from the flow cell in a background of 500 ppm $H_2$ in Ar. Times at which the gas composition was switched are indicated by arrows. Sensors were kept at 100° C. under a pressure of 1 atm. For this plot, zero bias has been set to the level equilibrated by 500 ppm $H_2$.

As another case study, it is useful to determine whether the presence of $O_2$ substantially alters the response behavior of uncoated and coated sensors. The $H_2$—$O_2$ system is the most-studied gas mixture on MIS devices due to its relevance for $H_2$ sensing in air. Water-forming reactions between adsorbed H and O on Pd consume the H in the device and generally cause a substantially decreased response on uncoated sensors M. Armgarth, D. Soderberg, I. Lundstrom, Palladium and platinum gate metal-oxide-semiconductor capacitors in hydrogen and oxygen mixtures Appl. Phys. Lett. 41 (1982) 654 ; M. Johansson, I. Lundstrom, L.-G. Ekedahl, Bridging the pressure gap for palladium metal-insulator-semiconductor hydrogen sensors in oxygen containing environments, J. Appl. Phys. 84 (1998) 44.; J. W. Medlin, R. Bastasz, A. H. McDaniel, Response of palladium metal-insulator-semiconductor devices to hydrogen-oxygen mixtures: comparisons between kinetic models and experiment, Sens. Actuators B 96 (2003) 290) as demonstrated in FIG. 6. In this case study, $O_2$ was added to the gas stream after sensor responses to 500 ppmH2 were stabilized. If the PI coating substantially prevented $O_2$ from accessing the surface, one would expect no effect of $O_2$ addition on the coated MIS response. Instead, FIG. 6 shows that $O_2$ in fact has a very large effect on the response of coated sensors. The coated sensor behaved similarly to the uncoated one but with a relatively more dramatic shift in sensor response and a slowed response time to both the addition and withdrawal of $O_2$ in the feed gas stream. The slower response of coated sensors is likely due to the slowed rate of $O_2$ diffusion through the coating layer before reaching the Pd surface. The results from coated sensors suggest that the PI-2555 layer does not prevent $O_2$ from diffusing to and adsorbing on the Pd surface. Again, this result is not surprising in terms of the finite permselectivity of the coating layer for $H_2$ over $O_2$; it is clear that the effect of $O_2$ on response is not dampened by the PI coating, and as in fact apparently enhanced.

It is interesting to note the apparently stronger effect of $O_2$ shifts on the coated MIS device compared to the uncoated devices (FIG. 6). The reaction of $O_2$ with $H_2$ permits $O_2$ to be classified as a "reactive gas" in the above discussion, and its permeability is significantly lower than $H_2$ in the PI membrane. However, the concentration of $O_2$ in the feed stream is almost 400 times greater than that of $H_2$, which may cause $O_2$ to more readily accumulate at the polymer-metal interface, thus, impacting response significantly. It is also not possible to preclude the possibility that the presence of PI at the metal surface increases the affinity of $O_2$ for the surface (resulting in less $H_2$ at the surface) or that the polymer-metal interface is more active for the oxidation reaction.

EXAMPLE 5

Coating Thickness Effect on Sensor Response

To examine how the PI-2555 thickness affects the coated sensor response, the same experiments on the effect of the contaminant gas mixture were conducted with coatings of measured thickness 92 and 2300 nm with the 670 nm coating. The results from the 92 nm coating layer behaved as those from an uncoated sensor (FIG. 3A); i.e., a coating of 92 nm could not prevent the contaminant gas from affecting the $H_2$ response. Although the 92 nm coating appeared to be uniform, it is possible that voids in the film could explain this behavior. It is also possible that a minimum film thickness is necessary to preclude hydrocarbon effects on sensor response, as discussed below. On the other hand, the 2300 nm coating thickness layer completely inhibited the contaminant gas effect on sensor response, but suffered a serious loss of sensitivity to $H_2$. The time to reach 90% of steady-state bias drop increased from 5 (670 nm) to 53 min (2300 nm). In other words, the coated sensor with 2300 nm coating thickness lost sensitivity to $H_2$. These coating thickness effects may also be explained by the solution-diffusion theory. As described by Koros and Fleming (W. J. Koros, G. K. Fleming, Membrane-based gas separation, J. Membr. Sci. 83 (1993) 1)., there are no continuous passages in effective solution-diffusion polymeric membranes. Instead, these membranes rely on the motion of chain segments consisting of polymer matrix. The motion may be agitated thermally and can generate transient gaps that only allow certain gases to pass (penetrants) from the upstream to the downstream face of the membrane. The penetrants advance via random jumps, but diffuse to the downstream face as a net result of a concentration gradient between the downstream and upstream face. With the increase of membrane thickness, the penetrants need to undergo more transient gaps. Consequently, the time for the penetrants to reach the downstream face increases. The ratio of response time for two different thicknesses is roughly proportional to the square of the thickness ratio as expected, indicating that response time is dictated by the characteristic diffusion time.

In light of this explanation, the failure of very thin polyimide films to prevent a contaminant gas effect on response may indicate that diffusion across thin PI films is sufficiently fast that a relatively high steady-state concentration is achieved on the "permeate" side of the film, and the sensor response is thus affected.

EXAMPLE 6

Sensor Measurements in an Oil Environment

The MIS ($Pd/SiO_2/n$-Si) capacitors were fabricated in a similar manner as described in Example 1. A layer of PI-2555 (DuPont HD Microsystems™) was coated onto the palladium surface using a spin coater (Specialty Coating Systems, Inc., Model P6708). A spin speed of 4500 rpm was used to obtain a final coating thickness of 670 nm as measured by ellipsometry (Modified J. A. Woollam; Stereoscope: Leica Model MZ6). The coated sensor was then cured at 100° C., 200° C. and 300° C. sequentially on a hot plate for 2 min, 30 min, and 30 min, respectively. Each sensor to be tested was glued on a TO header (Spectrum Semiconductor Materials, Inc.) using silver epoxy. Electrical leads for capacitance measurement were made by bonding the sensor bond pad to the poles on TO header. The sensor assembly was submerged in a flask filled with mineral oil (TJ|H₂b Analytic Services Inc.), which sits on a hot plate. Shifts in the C-V curve of each capacitor were measured using a program that records the voltage shift required to maintain a constant capacitance value at the inflection point of the C-V curve. Since the sensor response to $H_2$ is a negative-going signal, the addition of $H_2$ shifts the response to lower bias voltage. The baseline response was zeroed at the start of each experiment due to a baseline drift problem, which is well-known for Pd—$SiO_2$—Si sensors (Robins, I., Drift effects in transition-metal gate MOS and MISFETs, *Sens. Actuators B* 1993, 15, 238.). Except where noted otherwise, tests were performed with the oil held at 62° C. under atmospheric pressure.

Figure 7:
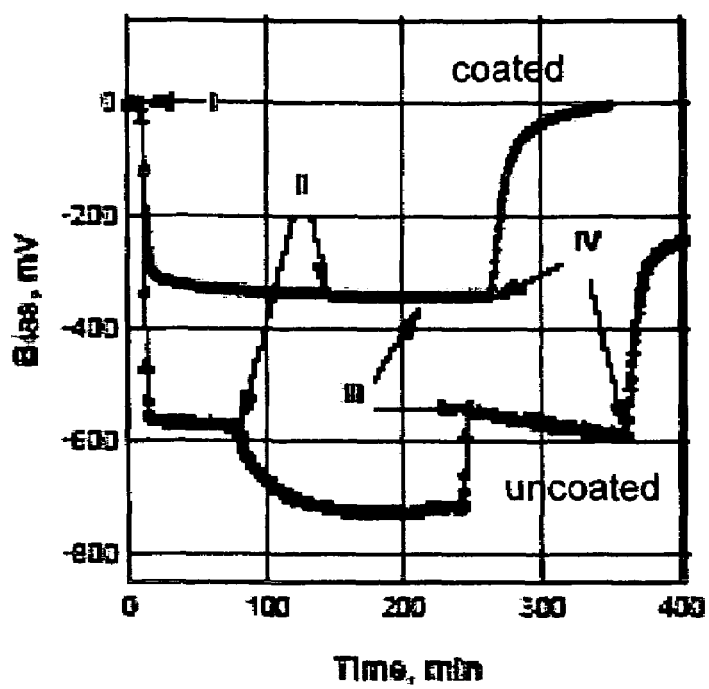
FIG. 7: Response of uncoated and coated sensors to $H_2$ and the contaminant gas mixture of Table 4 introduced in sequence to the transformer oil at the times indicated, in a background of 19% $O_2$ in $N_2$. Times at which the gas composition was switched are indicated by arrows (I. 4050 ppm $H_2$ in; II. Contaminant gas mixture in; III. Contaminant gas mixture out; IV. $H_2$ out). Sensors were kept at 62° C. under a pressure of 1 atm.

A gas mixture (Table 4) was used to assess sensitivity to small gases other than $H_2$ (referred to as the "contaminant gas" mixture hereafter). The composition in Table 4 was chosen because it represents typical gases and concentrations present in electrical transformer environments, where MIS sensors are targeted for application. Experiments were performed with 19% $O_2$ (on a volume basis) in the gas phase to simulate operation in air. Gases were introduced to the flask using mass flow controllers. All concentrations reported in this paper are for the gas-phase feed. Ostwald coefficients that describe the partitioning between the vapor and oil phase are listed in Table 4 (*IEC 60599 (Europe): Mineral Oil-Impregnated Electrical Equipment in Service—Guide to the Interpretation of Dissolved and Free Gases Analysis*, Second ed., 1999-2003) Gases were obtained as research purity (quoted as >99.9%) from Airgas. Nitrogen was used as diluent. The effects of adding $H_2$ and of adding the contaminant gas mixture were investigated on both uncoated and coated sensors. In the set of experiments described in FIG. 7, $H_2$ was bubbled into the oil first. For both devices, a large bias drop was generated due to the addition of $H_2$ to the oil. The coated sensor response to $H_2$ is slower as expected due to the time required for diffusion across the PI layer. Furthermore, there is no clear equilibration of the response for the uncoated devices in the oil phase. In fact, a slow drift with an apparent increase in response was repeatedly observed in numerous experiments. Using the same uncoated devices in gas-phase tests, such large-scale drifting is not observed. The $H_2$ response on the coated sensors equilibrates over intermediate periods of time in the oil phase, as clearly demonstrated in FIG. 7. FIG. 7 shows the response of uncoated and coated sensors to $H_2$ and the contaminant gas mixture (Table 4) introduced in sequence to the transformer oil at the times indicated, in a background of 19% $O_2$ in $N_2$. Times at which the gas composition was switched are indicated by arrows (I. 4050 ppm $H_2$ in; II. Contaminant gas mixture in; III. Contaminant gas mixture out; IV. $H_2$ out). Sensors were kept at 62° C. under a pressure of 1 atm.

These results suggest that the polyimide film may improve the stability of MIS response to dissolved gases, perhaps by discouraging decomposition of the oil ("coking") on the metal surface of the sensor. As a second step in the experiment described by FIG. 7, the contaminant gas mixture was added to the $H_2$ stream. A substantial bias decrease in uncoated sensor response resulted from the addition of contaminant gases to the $H_2$ stream. These results confirmed the cross-sensitivity of uncoated sensors to contaminant gases. In contrast, the coated sensor response was not appreciably altered by the addition of contaminant gas for the same operating conditions. Experiments conducted over run times as long as five days further confirmed that there were no effects due from contaminant gases. Although the mechanism by which the PI coating improved sensor performance is not completely understood, it appears to effectively inhibit accumulation of contaminant gases at the metal surface, and furthermore may prevent some "coking" reactions of the oil on the Pd surface that alter response.

Figure 8:
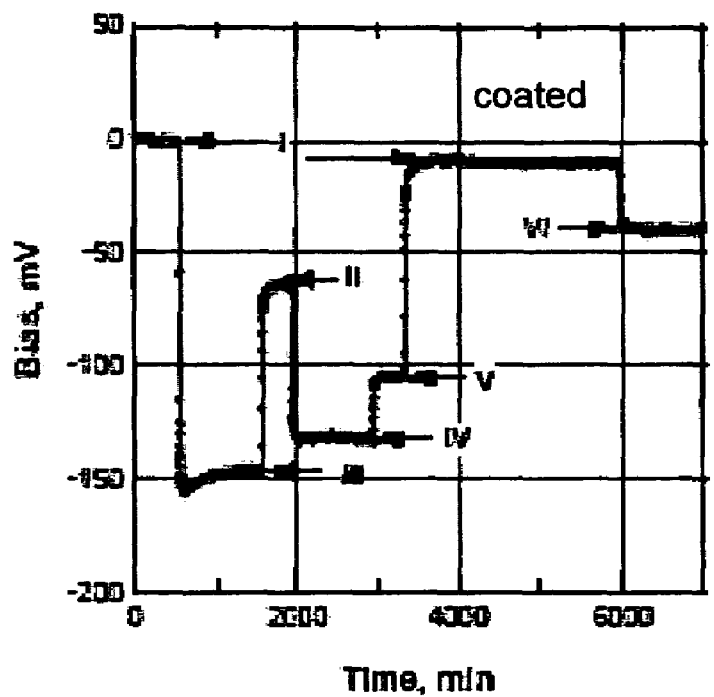
FIG. 8: Response of coated sensors to variation of $H_2$ concentration introduced in sequence to the transformer oil from 200 ppm to 8100 ppm (gas phase) at the times indicated, in a background of 19% $O_2$ in $N_2$. Times at which the gas composition was switched are indicated by arrows (I. 200 ppm $H_2$; II. 8100 ppm $H_2$; III. 1000 ppm $H_2$; IV. 6000 ppm $H_2$; V. 3000 ppm $H_2$; VI. 500 ppm $H_2$). Sensors were kept at 62° C. under a pressure of 1 atm.

Since the magnitude of bias drop is proportional to $H_2$ concentration in the transformer oil, it is important to investigate the sensitivity of the coated sensor to variation of $H_2$ concentration in the oil. Therefore, a set of experiments was conducted in which the $H_2$ concentration was varied in a random sequence from 8100 to 1000, 6000, 3000, 200 and 500 ppm (FIG. 8). FIG. 8 shows. response of coated sensors to variation of $H_2$ concentration introduced in sequence to the transformer oil from 200 ppm to 8100 ppm (gas phase) at the times indicated, in a background of 19% $O_2$ in $N_2$. Times at which the gas composition was switched are indicated by arrows (I. 200 ppm $H_2$; II. 8100 ppm $H_2$; III. 1000 ppm $H_2$; IV. 6000 ppm $H_2$; V. 3000 ppm $H_2$; VI. 500 ppm $H_2$). Sensors were kept at 62° C. under a pressure of 1 atm. The results demonstrate that the coated sensors were sensitive to changes in $H_2$ gas-phase concentrations over the range of 200 ppm to 8100 ppm, corresponding to oil-phase concentration changes of approximately 10 to 405 ppm (Table 1). Tests on $H_2$ gas feed concentrations as low as 10 ppm (0.5 ppm oil phase) indicate significant response even at very low oil concentrations (not shown). Thus, the $H_2$ sensitivity ranges at least from 0.5 to 405 ppm in the dissolved phase. This range spans from a satisfactorily operating transformer to one that needs investigation (*IEC 60599 (Europe): Mineral Oil-Impregnated Electrical Equipment in Service—Guide to the Interpretation of Dissolved and Free Gases Analysis*, Second ed., 1999-2003). Therefore, the PI-coated MIS sensors can successfully detect early fault formation in power transformers, and may be useful in other applications where dissolve $H_2$ needs to be detected with high selectivity. This example presents the use of polyimide-coated MIS sensor for selective detection of dissolved $H_2$. The coated sensor responds to the $H_2$ concentration variation in the wide of range of 0.5-405 ppm $H_2$ in the oil phase. These results showed the feasibility using PI coated sensors in power transformer fault detection and other industrial applications.

TABLE 4

Contaminant gas mixture composition and mean-value Ostwald coefficients describing the partitioning of gas between oil and gas phases.

| Gas | Gas feed concentration (ppm) | Ostwald coefficient at 20° C. | Ostwald coefficient at 50° C. |
| --- | --- | --- | --- |
| $C_2H_2$ | 200 | 1.2 | 0.90 |
| $C_2H_4$ | 400 | 1.7 | 1.4 |
| $C_2H_6$ | 400 | 2.4 | 1.8 |
| $CH_4$ | 2000 | 0.43 | 0.40 |
| CO | 3000 | 0.12 | 0.12 |
| $H_2$ | variable | 0.05 | 0.05 |
| $O_2$ | 190,000 | 0.17 | 0.17 |
| $N_2$ | balance | 0.09 | 0.09 |

LIST OF REFERENCES IN TABLE 2

1. Tanaka, K., Kita, H., Okano, M., and Okamoto, K., *Permeability and Permselectivity of Gases in Fluorinated and Non-Fluorinated Polyimides.* Polymer, 1992. 33(3): p. 585-592.
2. Tanaka, K., Kita, H., Okamoto, K., Nakamura, A., and Kusuki, Y., *Gas-Permeability and Permselectivity in*

*Polyimides Based on 3,3',4,4'-Biphenyltetracarboxylic Dianhydride.* Journal of Membrane Science, 1989. 47(1-2): p. 203-215.

3. Okamoto, K., Tanaka, K., Kita, H., Ishida, M., Kakimoto, M., and Imai, Y., *Gas-Permeability and Permselectivity of Polyimides Prepared from 4,4'-Diaminotriphenylamine.* Polymer Journal, 1992. 24(5): p. 451-457.

4. Tanaka, K., Okano, M., Toshino, H., Kita, H., and Okamoto, K. I., *Effect of Methyl Substituents on Permeability and Permselectivity of Gases in Polyimides Prepared from Methyl-Substituted Phenylenediamines.* Journal of Polymer Science Part B-Polymer Physics, 1992. 30(8): p. 907-914.

5. Stern, S. A., Mi, Y., Yamamoto, H., and Stclair, A. K., *Structure Permeability Relationships of Polyimide Membranes—Applications to the Separation of Gas-Mixtures.* Journal of Polymer Science Part B-Polymer Physics, 1989. 27(9): p. 1887-1909.

We claim:

1. A hydrogen sensor comprising:
   a. a semiconductor substrate;
   b. an insulator layer attached to the substrate;
   c. a layer of catalytic metal attached to the insulator layer; and
   d. a layer of hydrogen selective material attached to the catalytic metal layer wherein the layer of hydrogen selective material comprises a polyimide material, is between 200 nm and 1000 nm thick and is permeable to hydrogen and at least one other molecule.

2. The sensor of claim 1, wherein the thickness of the layer of hydrogen selective material is between 200 nm and 800 nm.

3. The sensor of claim 1, wherein the ideal $H_2/CO$ selectivity of the layer of hydrogen selective material is greater than 50.

4. The sensor of claim 3, wherein the ideal $H_2/CO$ selectivity is greater than 75.

5. The sensor of claim 1 wherein the layer of hydrogen selective material is permeable to hydrogen, carbon monoxide and at least one light hydrocarbon.

6. The sensor of claim 1, wherein the polyimide material is formed by polymerization of benzophenone tetracarboxylic dianhydride (BTDA) with a diamine selected from the group consisting of p,p' ODA (oxydianiline), p,m' ODA, m,m' ODA and combinations thereof.

7. The sensor of claim 1, wherein the polyimide material is formed by polymerization of BTDA with a first diamine selected from the group consisting of p,p' ODA, p,m' ODA, m,m' ODA and combinations thereof and a second diamine selected from the group consisting of p phenylenediamine (PDA) and m PDA.

8. The sensor of claim 7 wherein the polyimide material is formed by polymerization of BTDA with p,p' ODA and m PDA.

9. A method for detecting hydrogen concentration in a gaseous environment comprising a mixture of gases or a liquid environment comprising a mixture of gases dissolved in a liquid, wherein the mixture of gases comprises hydrogen and a second gas selected from the group consisting of light hydrocarbons and carbon monoxide, the method comprising the steps of:
   a. providing a metal-insulator-semiconductor (MIS) sensor capable of producing a greater change in sensor output due to a change in hydrogen concentration in the environment than the change in sensor output due to an equivalent change in concentration of a light hydrocarbon or carbon monoxide in the environment and capable of producing a change in sensor output due to a change in hydrogen concentration in the environment which is at least ten times greater than the change in sensor output due to an equivalent change in concentration of a light hydrocarbon in the environment, the sensor comprising a semiconductor substrate, a layer of insulator material attached to the substrate, a layer of catalytic metal attached to the layer of insulator material, and a layer of hydrogen selective material attached to the layer of catalytic material, wherein the layer of hydrogen selective material comprises a polyimide material, is between 200 nm and 1000 nm thick, and is permeable to hydrogen, carbon monoxide and at least one light hydrocarbon;
   b. exposing the hydrogen sensor to the environment; and
   c. detecting the output of the hydrogen sensor thereby detecting the hydrogen concentration in the environment.

10. The method of claim 9, wherein the thickness of the layer of hydrogen selective material is between 200 nm and 800 nm.

11. The method of claim 9, wherein the ideal $H_2/CO$ selectivity of the layer of hydrogen selective material is greater than 50.

12. The method of claim 9 wherein the polyimide material is formed by polymerization of benzophenone tetracarboxylic dianhydride (BTDA) with a diamine selected from the group consisting of p,p' ODA (oxydianiline), p,m' ODA, m,m' ODA and combinations thereof.

13. The method of claim 9, wherein the second gas is a light hydrocarbon.

14. The method of claim 13, wherein the second gas is selected from the group consisting of methane, ethylene, and acetylene.

15. The method of claim 13, wherein the gas mixture further comprises oxygen and the oxygen content of the gas mixture does not vary by greater than 10%.

16. The method of claim 13, wherein the gas mixture further comprises carbon monoxide.

17. The method of claim 9, wherein the change in sensor output due to a change in hydrogen concentration in the environment is at least 400 times greater than the change in sensor output due to a subsequent change in concentration of the second gas, wherein the second gas is selected from the group consisting of methane, ethylene, acetylene, and carbon monoxide.

18. The method of claim 9 wherein the sensor is exposed to the environment by exposing the hydrogen selective material to a gas mixture.

19. The method of claim 9, wherein the sensor is exposed to the environment by exposing the hydrogen selective material to an oil comprising a mixture of dissolved gases.

20. A method for making a hydrogen selective metal-insulator-semiconductor (MIS) hydrogen sensor comprising the steps of:
   a. providing a MIS sensor comprising a semiconductor substrate, a layer of insulator material attached to the substrate, a layer of catalytic metal attached to the layer of insulator material; and
   b. coating the layer of catalytic metal with a layer of hydrogen selective material wherein the layer of hydrogen selective material comprises a polyimide material, is between 200 nm and 1000 nm thick and is permeable to hydrogen and at least one other molecule.

21. The method of claim 20 wherein the thickness of the layer of hydrogen selective material is between 200 nm and 800 nm.

22. The sensor of claim 20 wherein the polyimide material is formed by polymerization of benzophenone tetracarboxylic dianhydride (BTDA) with a diamine selected from the group consisting of p,p' ODA (oxydianiline), p,m' ODA, m,m' ODA and combinations thereof.

23. The method of claim 20, wherein the ideal $H_2/CO$ selectivity of the layer of hydrogen selective material is greater than 50.

* * * * *